United States Patent
Galili et al.

(10) Patent No.: US 10,092,586 B2
(45) Date of Patent: Oct. 9, 2018

(54) GLYCOLIPID CONTAINING COMPOSITIONS FOR USE IN THE TREATMENT OF TUMORS

(71) Applicant: Agalimmune Limited (GB/GB), London (GB)

(72) Inventors: Uri Galili, Irvine, CA (US); Christopher Pickford, London (GB); Graham John Charles Griffiths, London (GB)

(73) Assignee: Agalimmune Limited (GB)

( * ) Notice: Subject to any disclaimer, the term of this patent is extended or adjusted under 35 U.S.C. 154(b) by 45 days.

(21) Appl. No.: 15/310,074

(22) PCT Filed: May 8, 2015

(86) PCT No.: PCT/GB2015/051368
§ 371 (c)(1),
(2) Date: Nov. 9, 2016

(87) PCT Pub. No.: WO2015/170121
PCT Pub. Date: Nov. 12, 2015

(65) Prior Publication Data
US 2017/0266214 A1    Sep. 21, 2017

Related U.S. Application Data

(60) Provisional application No. 61/991,060, filed on May 9, 2014.

(51) Int. Cl.
*A61K 31/7032* (2006.01)
*A61K 45/06* (2006.01)
*A61K 9/00* (2006.01)

(52) U.S. Cl.
CPC ........ *A61K 31/7032* (2013.01); *A61K 9/0014* (2013.01); *A61K 45/06* (2013.01)

(58) Field of Classification Search
None
See application file for complete search history.

(56) References Cited

FOREIGN PATENT DOCUMENTS

| WO | 95/24924 A1 | 9/1995 |
|----|-------------|--------|
| WO | 2006/091515 A2 | 8/2006 |

OTHER PUBLICATIONS

Whalen et al., Anticancer Research (2012), 32, pp. 3861-3868.*
Blake et al., Journal of Visualized Experiments (2011), 54, e3289, pp. 1-9.*
Galili Uri: "Conversion of tumors into autologous vaccines by intratumoral injection of [alpha]-Gal glycolipids that induce anti-Gal/[alpha]-Gal epitope interaction.", Clinical & Developmental Immunology 2011, vol. 2011, 134020, 2011, 0pages 1-10, XP002741566, ISSN: 1740-2530.
KODE Biotech biosurface Innovation: "FSL-Galili (GALa3GALb4GLCNb)-SA1-L1", KODE Biotech—KODE Products, 2012, XP002741567, Retrieved from the Internet: URL:http://kodebiotech.com/sales/products/product_info.php?id-49&cat=carb [retrieved on Jun. 30, 2015].
PCT/GB2015/051368 International Search Report, dated Jul. 14, 2015.
Galili et al., Intratumoral Injection of a-gal Glycolipids Induces Xenograft-Like Destructin and Conversion of Lesions into Endogenous Vaccines, J Immunol 2007; 178:4676-4687, 2007.
Carlson et al., Selective Tumor Cell Targeting Using Low-Affinity, Multivalent Interactions, ACS Chemical Biology vol. 2 No. 2 pp. 119-127, Feb. 9, 2007.
Wang et al, Enhanced Inhibition of Human Anti-Gal Antibody Binding to Mammalian Cells by Synthetic a-Gal Epitope Polymers, American Chemical Society, J. Am. Chem. Soc. 1999, 121, 8174-8181.

* cited by examiner

*Primary Examiner* — Brian J Davis
(74) *Attorney, Agent, or Firm* — Hahn Loeser & Parks, LLP—San Diego

(57) ABSTRACT

The invention relates to pharmaceutical compositions comprising α-Gal BOEL for use in treating patients with tumors. The invention also relates to methods of treating tumors using said compositions. The invention discloses that following intratumoral injection of α-Gal BOEL, binding of the natural anti-Gal antibody to de novo expressed tumoral α-Gal epitopes induces inflammation resulting in an anti-Gal antibody mediated opsonization of tumor cells and their uptake by antigen presenting cells. These antigen presenting cells migrate to draining lymph nodes and activate tumor specific T cells thereby converting the treated tumor lesions into in situ autologous tumor vaccines. This therapy can be applied to patients with multiple lesions and in neo-adjuvant therapy to patients before tumor resection. In addition to the regression and/or destruction of the treated tumor, such a vaccine will help in the immune mediated destruction of micrometastases that are not detectable during the removal of the treated tumor. The invention further teaches the enhancement of anti-tumor α-Gal BOEL treatment by the use of antibodies that inhibit the activity of immunological checkpoints molecules.

18 Claims, 8 Drawing Sheets

A

B

C
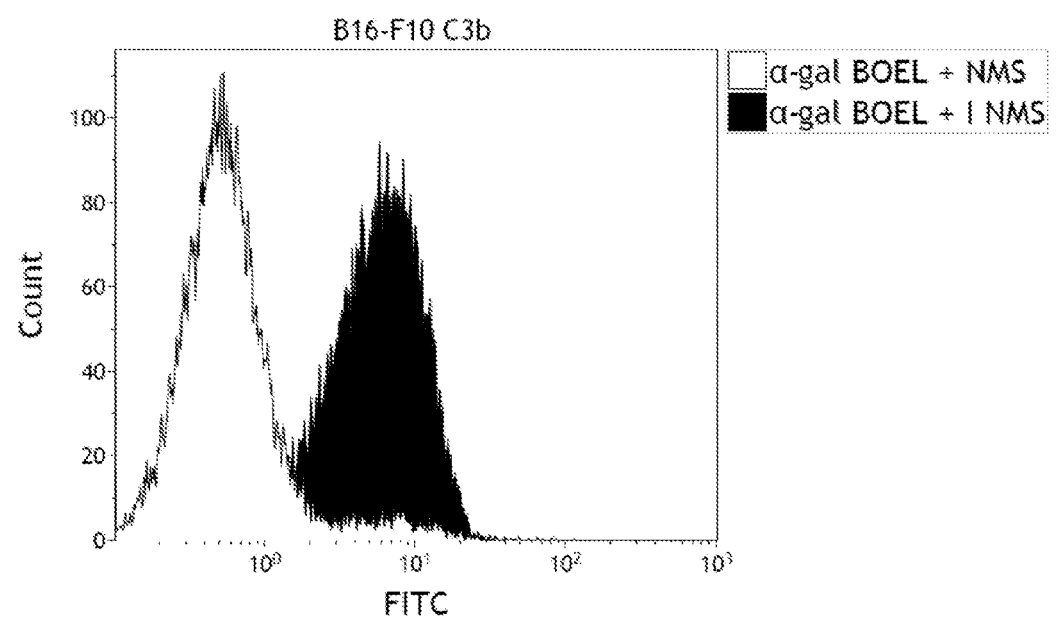
D
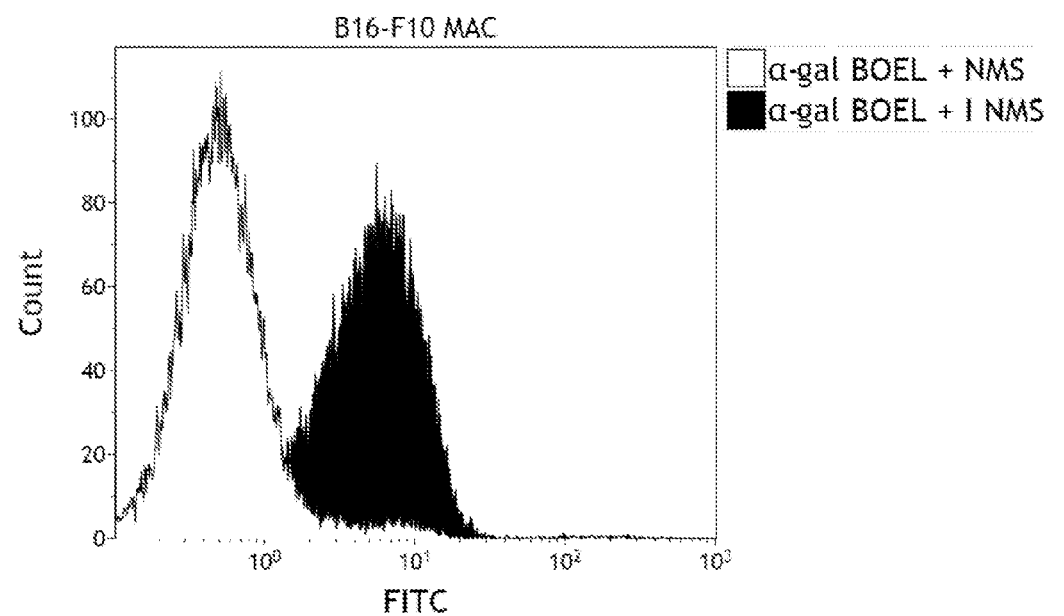
FIGURE 6 (ctd)

GLYCOLIPID CONTAINING COMPOSITIONS FOR USE IN THE TREATMENT OF TUMORS

CROSS-REFERENCE TO RELATED APPLICATIONS

The present application is a U.S. National Stage entry under 35 U.S.C. § 371 of International Application No. PCT/GB2015/051368 filed on May 8, 2015, designating the United States of America and published in English on Nov. 12, 2015, which in turn claims priority to U.S. Provisional Application 61/991,060 filed on May 9, 2014, each of which is hereby incorporated by reference in its entirety.

FIELD OF THE INVENTION

The invention relates to pharmaceutical compositions comprising the α-Gal glycolipid (9Z,9'Z)-(2R)-3-(((2-(6-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexanamido)ethoxy)(hydroxy)phosphoryl)oxy)propane-1,2-diyl bis(octadec-9-enoate) (α-Gal BOEL) for use in treating tumours. The invention also relates to methods of treating tumours using said compositions.

BACKGROUND OF THE INVENTION

The major cause of death in cancer patients with solid tumours is the recurrence of the cancer after surgery as multiple metastases are non-resectable and/or refractory to any therapy. The majority of these patients are considered to have a terminal cancer disease. As no treatment is available for them, many of these patients die within weeks or a few months after detection of metastatic tumour lesions.

Tumours develop in cancer patients because the immune system fails to detect tumour cells as cells that ought to be destroyed. Tumour cells express autologous tumour antigens in a large proportion of cancer patients. These autologous tumour antigens may elicit a protective anti-tumour immune response. Tumour cells, or tumour cell membranes, have to be internalized by antigen presenting cells in order to induce the development of an anti-tumour immune response. However, the immune system in cancer patients displays "ignorance" toward the tumour antigens that is associated with early development of the tumour in a "stealthy" way, so it is "invisible" to antigen presenting cells (Pardoll D M. Clin. Immunol. 2000; 95:S44-49; and Dunn G P et al. Nat Immunol 2002; 3: 991-8).

In addition, the tumour microenvironment and local cytokine milieu are often suppressive toward immune function and can actively induce immune cell anergy and death (Malmberg K J. Cancer Immunol. Immunother. 2004; 53: 879-92; Lugade A A et al. J. Immunol. 2005; 174: 7516-23). Effective treatment of such metastatic tumour lesions requires two components:

1. Destruction of the lesions that are large enough to be detected visually or by imaging technology, and
2. Induction of a protective anti-tumour immune response against tumour antigens.

Such an immune response results in immune-mediated detection, regression, and/or destruction of micrometastases which cannot be detected visually and are not detectable by imaging.

Induction of a protective anti-tumour immune response requires uptake of the tumour cells or cell membranes by antigen presenting cells and their transportation to the draining lymph nodes, where the antigen presenting cells process the tumour antigen molecules. The majority of these tumour antigens are specific to the individual patient. The immunogenic tumour antigen peptides are presented by antigen presenting cells in association with class I or class II MHC molecules for the activation of tumour specific $CD8^+$ and $CD4^+$ T cells, respectively. Only after these T cells are activated by the processed and presented tumour antigen peptides, can these lymphocytes proliferate, leave the lymph nodes, circulate in the body, seek and destroy metastatic tumour cells expressing tumour antigens. In addition, though only after they are activated, helper T cells can provide help to B cells for producing antibodies against the tumour antigens. However, since the tumour cells naturally evolve to be "invisible" to antigen presenting cells, the developing tumour metastases are usually ignored by the immune system to the extent that metastasizing tumour cells can proliferate even within lymph nodes. Therefore, eliciting an effective anti-tumour immune response requires effective targeting of tumour cells to antigen presenting cells.

What is needed are compositions and methods to introduce compounds into a tumour, such as by non-surgical or surgical methods, under conditions such that the compound will insert into tumour cell membranes and a naturally occurring antibody will interact with the introduced compound. It is believed that such interaction will induce local inflammation for the regression and/or destruction of the tumour and the targeting tumour cells and/or tumour cell membranes to antigen presenting cells. This process will elicit a protective immune response in the host against tumour cells expressing the tumour antigens in micrometastases that cannot be detected visually or by imaging and therefore cannot be removed by resection.

US 2006/251661 describes methods of administering natural glycolipid compounds to tumour lesions that induce local expression of α-Gal epitopes within the tumour which interact with the natural anti-Gal antibody.

There is therefore a need to provide an improved method of incorporating α-Gal molecules into a tumour in order to activate an anti-Gal mediated immune response against the tumour, there is also a need for novel pharmaceutical compositions that facilitate this method.

SUMMARY OF THE INVENTION

According to a first aspect of the invention, there is provided a pharmaceutical composition comprising (9Z,9'Z)-(2R)-3-(((2-(6-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexanamido)ethoxy)(hydroxy)phosphoryl)oxy)propane-1,2-diyl bis(octadec-9-enoate) (α-Gal BOEL) for use in the treatment of a tumour.

According to a further aspect of the invention there is provided a pharmaceutical composition comprising α-Gal BOEL in combination with one or more additional therapeutic agents.

According to a further aspect of the invention, there is provided a method of treating a tumour in a subject, comprising:

a) providing:
   i) a subject comprising at least one tumour that comprises a plurality of cancer cells having a cell surface; and
   ii) the pharmaceutical composition as defined herein; and
b) introducing the pharmaceutical composition into the tumour.

The therapeutic use of α-Gal BOEL has not previously been described in the art, nor the specific use to treat tumours. It was previously thought that α-Gal glycolipids with complex and lengthy carbohydrate chains were necessary in order to induce an immune response (for example, as described in the Examples of US 2006/251661 and Galili et al, *The Journal of Immunology*, 2007, 178:4676-4687).

These complex carbohydrates, derived from a natural source of rabbit blood erythrocytes comprise an unfractionated mixture of α-Gal glycolipids, each containing the α-Gal epitope. The microheterogeneity that results from glycan biosynthesis, coupled with the unseparable mixture of compounds that results from extraction renders complex and difficult to scale material (Galili et al (2007), supra).

However, the inventors have surprisingly found that single molecules containing an α-Gal glycolipid with short carbohydrate chains (such as the short carbohydrate 'Functional' group of α-Gal BOEL) are effective in treating tumours and have the added benefits of ease of production, storage and administration.

It is also believed that α-Gal BOEL has increased water solubility thereby easing formation for injection. Without being bound by theory, it is thought that the spacer component of α-Gal BOEL improves the molecule's solubility.

Data is presented herein which demonstrates a number of beneficial properties for the use of α-Gal BOEL in the treatment of tumours. For example, α-Gal BOEL demonstrates effective binding to anti-Gal antibodies (see Example 1 and FIG. 2). In addition, α-Gal BOEL demonstrates efficacious properties by inducing complement mediated cell lysis of cancer cells (see Example 2 and FIG. 3) and that viability of cells is not impacted in the absence of complement (see Example 2 and FIG. 4) and α-Gal BOEL can be effectively incorporated into tumour cells (see Example 2 and FIG. 5). In addition, incorporation of α-Gal BOEL leads to deposition of complement proteins onto tumour cells (Example 3 and FIG. 6). Furthermore, α-Gal BOEL demonstrates induction of a protective anti-tumour immune response against development of distant metastases in an in vivo efficacy model. This effect is dependent on the presence of anti-Gal in the treated subject. In the absence of anti-Gal, no significant protective anti-tumour immune response is observed (see Example 4 and FIGS. 7 and 8). In addition, α-Gal BOEL and anti-PD-1 antibody combinations show superior in vivo activity over anti-PD-1 antibodies alone (see Example 5 and FIG. 9).

DETAILED DESCRIPTION OF THE INVENTION

Figure 1:
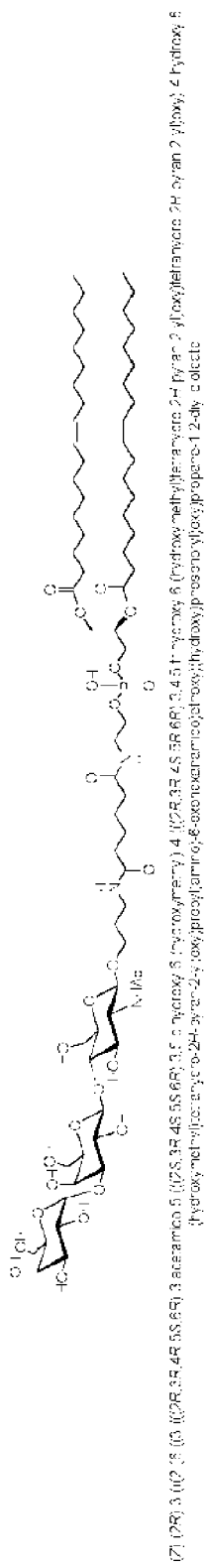
FIG. 1: The structure of α-Gal BOEL.

The invention described herein provides a composition and method that enables α-Gal glycolipids (i.e. α-Gal BOEL) to be inserted into the cell membrane of tumour cells within a treated tumour. It is believed that the presence of α-Gal glycolipids in the tumour lesion results in the destruction or regression of the tumour by the immune mediated inflammatory process that is induced by the interaction between the natural anti-Gal antibodies present in the subject and the α-Gal epitope of α-Gal BOEL. Moreover, this treatment converts the treated tumour into a vaccine that elicits a systemic protective anti-tumour immune response that prevents the development of distant metastases by immune destruction of metastatic tumour cells.

The invention described herein comprises a therapy treatment modality that includes, but is not limited to, intratumoural delivery of a specific glycolipid, referred to as α-Gal BOEL, that carries the α-Gal epitope and therefore may be referred to as an "α-Gal glycolipid". The α-Gal glycolipid inserts into the outer leaflet of the cell membrane of tumour cells within the treated lesion. The presence of α-Gal glycolipids in the tumour lesion achieves two goals:

1. Immune mediated destruction of tumour lesions by the inflammatory process that is induced within the tumour lesion by the interaction between the natural anti-Gal antibody and the α-Gal epitopes of α-Gal glycolipids inserted in tumour cell membranes; and
2. Effective uptake by antigen presenting cells of tumour cells and tumour cell membranes with inserted α-Gal glycolipids and thus, expressing α-Gal epitopes that bind in situ anti-Gal antibodies, thereby converting the treated tumour lesion into an autologous tumour vaccine.

Although it is not necessary to understand the mechanism of an invention, it is believed that this uptake results in an effective immune response against tumour antigens present on or within the tumour cells expressing α-Gal epitopes. It is further believed that this immune response may result in immune mediated destruction of metastatic tumour cells that do not express α-Gal epitopes, but express the tumour antigen.

The invention contemplates administering by injection, or any other means, compounds into tumours that induce expression of α-Gal epitope on cells within the treated tumour. Such administration of α-Gal glycolipids achieves the following objectives:

1. The binding of the natural anti-Gal antibody to α-Gal epitopes of α-Gal glycolipids may result in local complement activation, thereby generating chemotactic factors including, but not limited to, C5a and C3a. These chemotactic factors induce an extensive migration of antigen presenting cells such as, but not limited to, dendritic cells and macrophages into the tumour tissue.
2. The lipid tails of α-Gal glycolipids will spontaneously insert into the tumour cell membranes within the treated lesion, resulting in expression of α-Gal epitopes on tumour cells. Anti-Gal binding to these epitopes is believed to induce regression and/or destruction of tumours comprising tumour cells.
3. Opsonization of the tumour cell membranes by anti-Gal targets them for effective uptake by antigen presenting cells that migrate into the tumour. The migration of these antigen presenting cells is directed by the chemotactic complement cleavage peptides that are generated following anti-Gal binding to α-Gal glycolipids within the treated tumour.

Without being bound by any particular mechanism, it is believed that the Fc portion of the tumour cell membrane-bound anti-Gal IgG molecules binds to Fc-gamma receptors (FcγR) on antigen presenting cells and induces uptake of the tumour cells by the antigen presenting cells. A similar induction for uptake may occur as a result of the interaction between the C3b component of complement deposits on anti-Gal binding tumour cells and C3b receptors on antigen presenting cells. This anti-Gal mediated targeting of tumour membranes to antigen presenting cells enables effective transport of autologous tumour antigens to draining lymph nodes, and processing and presentation of immunogenic tumour antigen peptides by antigen presenting cells within the lymph nodes.

Thus, intratumoural injection of α-Gal glycolipids converts a treated tumour lesion into an in situ autologous tumour vaccine that provides tumour antigens to the immune system, thereby eliciting a protective anti-tumour immune response. This immune response is capable of inducing tumour regression comprising the destruction of individual tumour cells or of small aggregates of tumour cells (i.e. for example, micrometastases). These micrometastases are usually undetectable either visually or by imaging and not accessible by conventional surgical or radiotherapy techniques (i.e. they are nonresectable because of their small size). Therefore, the present method has the added advantage that it is able to treat micrometastases which are usually undetectable either visually or by imaging and not accessible by conventional surgical and radiotherapy techniques.

DEFINITIONS

References herein to the term "α-Gal BOEL" refer to a specific example of α-Gal glycolipid such as an α-Gal bridged bis-octadecenoate lipid which has the structure shown in FIG. 1 and the full chemical name (according to IUPAC convention) of (9Z,9'Z)-(2R)-3-(((2-(6-(((3-(((2R,3R,4R,5S,6R)-3-acetamido-5-(((2S,3R,4S,5S,6R)-3, 5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexanamido)ethoxy)(hydroxy)phosphoryl)oxy) propane-1,2-diyl bis(octadec-9-enoate).

α-Gal BOEL is commercially available from Sigma-Aldrich under the product name 'FSL-Galili(tri)™' (Catalogue No. F9432). This construct consists of a functional (F), spacer (S) and lipid (L) component and can be used to insert into cell membranes so that the cell will display the functional (F) component on its surface. The functional component of α-Gal BOEL is a trisaccharide group of: Gal-α1-3-Gal-β1-4GlcNAc (i.e. the α-Gal epitope). The spacer component is a O(CH$_2$)$_3$NH group and the lipid component is an adipate derivative (i.e. OOC(CH$_2$)$_4$COO, the ionized form of adipic acid) of dioleoylphosphatidylethanolamine (DOPE).

The term "α-Gal epitopes", as used herein, refers to any molecule, or part of a molecule, with a terminal structure comprising Galα1-3Galβ1-4GlcNAc-R, Galα1-3Galβ1-3GlcNAc-R, or any carbohydrate chain with terminal Galα1-3Gal at the non-reducing end. The α-Galactosyl (also referred to as "alpha-Gal" or "α-Gal") epitope, galactosyl-alpha-1,3-Galactosyl-beta-1,4-N-acetylglucosamine is described in Galili, U. and Avila, J. L., Alpha-Gal and Anti-Gal, Subcellular Biochemistry, Vol. 32, 1999. Xenotransplantation studies have determined that humans mount an immune response to the α-Galactosyl epitope, which itself is not normally found in humans, but is found in other animals and many microorganisms.

The term "glycolipids", as used herein, refers to any molecule with at least one carbohydrate chain linked to a ceramide, a fatty acid chain, or any other lipid. Alternatively, a glycolipid maybe referred to as a glycosphingolipid. In one embodiment, the glycolipid is an adipate derivative of dioleoylphosphatidylethanolamine (DOPE).

The term "anti-Gal" as used herein, refers to naturally occurring antibodies which bind the α-Gal epitope.

The term "α-1,3-Galactosyltransferase" as used herein, refers to any enzyme capable of synthesizing α-Gal epitopes.

The term "anti-Gal binding epitope", as used herein, refers to any molecule or part of a molecule that is capable of binding, in vivo or in vitro, the natural anti-Gal antibody.

The term "nonresectable", as used herein, refers to any part of an organ or bodily structure that cannot be surgically removed. For example, a "nonresectable tumour" may be a tumour physically unreachable by conventional surgical techniques, a tumour where its removal does not improve the overall cancer disease or wellbeing of the patient, or a tumour where its removal may be detrimental to a vital organ.

The term "membrane-bound", as used herein, refers to any molecule that is stably attached to, or embedded within, a phospholipid bilayer. Such attaching or embedding may involve forces including, but not limited to, ionic bonds, covalent bonds, hydrophobic forces, or Van der Waals forces etc. For example, a protein comprising a hydrophobic amino acid region may insert itself into a phospholipid bilayer membrane, or a molecule that contains a lipid tail can insert itself into the phospholipid bilayer of cells and become embedded. The lipid component of α-Gal BOEL is used to insert into the cell membranes of the tumour to create a tumour displaying the α-Gal epitope on its cell surface.

The term "subset", as used herein, refers to a specialized group lower in number than the whole group. For example, a patient may present with a plurality of nonresectable solid tumours. Of this plurality, a subset may be accessible by non-surgical techniques whereas another subset may not be accessible by non-surgical techniques.

The term "accessible", as used herein, refers to any ability to treat a solid tumour by non-surgical techniques. Such techniques may include, but are not limited to, injection into the skin or injection via endoscopy, bronchoscopy, cystoscopy, colonoscopy, laparoscopy, catheterization, or topical application by a lotion, ointment or powder. For example, an ovarian solid tumour may be accessible by laparoscopy. In another example, a colon solid tumour may be accessible by colonoscopy.

The term "introducing", as used herein, refers to any method of transferring a compound into a tissue and subsequently into cells within said tissue. Such methods of introduction may include, but are not limited to, viral vectors, retroviral vectors, adenoviral vectors, biobalistics, lipofection, and many commercially available DNA vectors known in the art. Alternatively, a compound may be placed adjacent to a cell such that the compound is incorporated into the cell by physiological mechanisms (i.e., for example, hydrophobic interactions or active transport). One method of introduction comprises injection, wherein a compound is placed directly into the intercellular space within the injected tissue. Such an injection may be possible when an organ part, growth (i.e., for example, a solid tumour), or bodily cavity is "accessible".

The term "into", as used herein, refers to the successful penetration of a molecule through or within a cell membrane. For example, a viral vector may be introduced into a solid tumour cell under conditions such that the tumour cell is transfected. In another example, a glycolipid may be introduced into a tumour cell under conditions such that the glycolipid becomes inserted into the cell's phospholipid bilayer membrane.

The terms "regression", "is at least partially diminished in size" or "reduced", as used herein, refer to a diminution of a bodily growth, such as, for example, a solid tumour. Such a diminution may be determined by a reduction in measured parameters such as, but not limited to, diameter, mass (i.e., weight), or volume. The diminution by no means indicates that the size is completely reduced, only that a measured parameter is quantitatively less than a previous determination.

The term "destruction", as used herein, refers to the complete cellular breakdown of a bodily growth, such as, for example, a solid tumour. Such destruction may involve intracellular apoptosis, T cell mediated killing of cells, complement mediated cytolysis, and/or macrophage phagocytosis such that the bodily growth is completely digested and eliminated from the body. The term "destruction of a tumour" refers to the reduction of a tumour to such a degree that it is no longer detectable by diagnostic means.

The term "treating", "treatment" and "treat" all used herein are intended to refer to a procedure which results in at least partially diminishing in size or reduction in size of a bodily growth, such as, for example, a solid tumour.

The term "fewer than all", as used herein, refers to a subset of a group. In the context of one embodiment of the present invention, treatment of fewer than all of the tumours in a patient is contemplated. In other words, in one embodiment, it is not necessary to treat every tumour by introduction of the α-Gal epitope (e.g. by introduction of α-Gal BOEL); rather, introduction to a subset results in an immune response to all tumours (including those not directly treated). In this manner, one can achieve a collective diminution of a plurality of bodily growths, such as, for example, solid tumour metastases. Such a diminution may be determined by a reduction in measured parameters such as, but not limited to, number. The diminution by no means indicates that the parameter is reduced to zero, only that a measured parameter is quantitatively less than a previous determination.

The term "growth", as used herein, refers to any tissue or organ that comprises a cellular mass considered to represent an abnormal proliferation. Such growths may be cancerous, non-cancerous, malignant, or non-malignant. If a growth comprises cancer, it may be a tumour.

The term "tumour" as used herein, refers to an abnormal mass of tissue which results from an abnormal growth or division of cells. Such tumours may be solid (i.e. a mass of cells in particular organ, tissue or gland, such as on the peritoneum, liver, pancreas, lung, urinary bladder, prostate, uterus, cervix, vagina, breast, skin, brain, lymph node, head and neck, stomach, intestine, colon or ovaries) or non-solid (i.e. liquid tumours which develop in the blood, such as leukaemia).

The term "subject", as used herein, refers to any organism that is capable of developing a tumour. Such organisms include, but are not limited to, mammals, humans, non-primate mammals, prosimians and New World monkeys etc.

The term "molecule", as used herein, refers to the smallest particle of a composition that retains all the properties of the composition and is composed of one or more atoms. These one or more atoms are arranged such that the molecule may interact (i.e., ionically, covalently, non-covalently etc.) with other molecules to form attachments and/or associations. For example, a molecule may have one or more atoms arranged to provide a capability for an interaction with an anti-Gal antibody.

Natural Anti-Gal Antibody, α-Gal Epitope, and Xenograft Rejection

Anti-Gal is believed to be a natural antibody that may be present in all humans, constituting 0.1-2% of serum immunoglobulins (Bovin N. V., Biochemistry (Moscow), 2013;

78(7):786-797, Galili et al. *J. Exp. Med.* 1984; 160: 1519-31, and Hamadeh R M et al. *Clin. Diagnos. Lab. Immunol.* 1995; 2:125-31). Studies have presented data indicating that anti-Gal antibodies might interact specifically with α-Gal epitopes on cell surface or free glycolipids and glycoproteins. (Galili U et al. *J. Exp. Med.* 1985, 162: 573-82, and Galili U. *Springer Semin Immunopathol.* 1993; 15: 155-171). It is further reported that the anti-Gal antibody may be produced throughout life as a result of antigenic stimulation by bacteria of the gastrointestinal flora (Galili U et al. *Infect. Immun.* 1988; 56: 1730-37).

The α-Gal epitope can be abundantly bio-synthesized on glycolipids and glycoproteins by the glycosylation enzyme α1,3galactosyltransferase within the Golgi apparatus of cells of non-primate mammals, prosimians and in New World monkeys (Galili U et al. *Biol. Chem.* 1988; 263; 17755-62). In contrast, humans, apes, and Old World monkeys lack α-Gal epitopes, but produce the natural anti-Gal antibody in very large amounts (Galili U et al. *Proc. Natl. Acad. Sci. USA* 1987, 84: 1369-73). Based on the sequence of the α1,3galactosyltransferase pseudogene in monkeys and apes, it was estimated that the α1,3galactosyltransferase gene was inactivated in ancestral Old World primates approximately 20 million years ago (Galili U, Swanson K. *Proc. Natl. Acad. Sci. USA* 1991; 88: 7401-04). It was suggested that this evolutionary event was associated with the appearance of an infectious microbial agent, endemic to the Old World (i.e. currently Europe, Asia and Africa), which was detrimental to primates and which expressed α-Gal epitopes. Primates could produce anti-Gal as a protective antibody against such putative detrimental agent, only after they evolved under a selective pressure for the inactivation of the α1,3galactosyltransferase gene and thus, loss of immune tolerance to the α-Gal epitope (Galili U, Andrews P. J. *Human Evolution* 29:433-42, 1995).

The strong protective activity of the natural anti-Gal antibody has been evolutionarily conserved in humans and monkeys. This can be inferred from xenotransplantation studies with pig organs expressing α-Gal epitopes. Since cells of various mammals, including pigs, express α-Gal epitopes, organs from pigs transplanted in humans, or in Old World monkeys, are rejected because of the in vivo binding of the anti-Gal antibody to these epitopes on pig cells (Galili, U. *Immunol. Today* 1993, 14: 480-82). Transplantation of pig tissues into humans or into Old World monkeys results in avid anti-Gal binding to α-Gal epitopes on an in vivo graft and the subsequent induction of the xenograft rejection. Vascularized xenografts (e.g. pig heart) undergo rapid rejection (called hyperacute rejection) in monkeys within 30-60 minutes mostly as a result of anti-Gal antibody molecules binding to α-Gal epitopes on pig endothelial cells, activation of complement, lysis of the endothelial cells, and collapse of the vascular bed (Collins B H et al. *J. Immunol.* 1995; 154: 5500-10). In addition, much of the destruction of xenograft cells in extravascular areas is mediated by anti-Gal IgG binding to α-Gal epitopes on various cells. This binding results in antibody dependent cell mediated cytolysis (ADCC), following the binding of the Fc portion of anti-Gal IgG to cell bound Fcγ receptors on granulocytes, macrophages, and NK cells.

The anti-Gal mediated destruction of xenografts could be monitored with pig cartilage (an avascular xenograft tissue) transplanted into rhesus monkeys (i.e. monkeys that naturally produce anti-Gal antibodies). Studies indicate that the binding of anti-Gal to α-Gal epitopes in the pig tissue results in induction of an extensive inflammatory reaction that leads to gradual destruction of the tissue within 2 months (Stone K R et al. *Transplantation* 1998, 65: 1577-83). Binding of anti-Gal to α-Gal epitopes on the cartilage cellular and extracellular matrix glycoproteins further opsonizes them (i.e., forms immune complexes with them) and thus, targets them to antigen presenting cells by the binding of the Fc portion of the immuno-complexed anti-Gal to Fcγ receptors on antigen presenting cells. The antigen presenting cells, in turn, transport these pig glycoproteins to draining lymph nodes where they activate the many T cells specific to the multiple pig xenopeptides. These activated T cells subsequently migrate into the cartilage xenograft implant and comprise approximately 80% of the infiltrating mononuclear cells. That this inflammatory response is primarily mediated by anti-Gal interaction with α-Gal epitopes can be inferred from monitoring the immune response to the pig cartilage xenograft from which the α-Gal epitopes were removed by an enzymatic treatment (for example, using recombinant α-Galactosidase). α-Galactosidase destroys the α-Gal epitopes on the cartilage glycoproteins by cleaving (hydrolyzing) the terminal α-Galactosyl unit. In the absence of α-Gal epitopes on the pig cartilage glycoproteins, there is no anti-Gal binding to the xenograft, and thus, no effective antigen presenting cell mediated transport of the xenoglycoproteins occurs. This is indicated by a lack of significant T cell infiltration in a xenograft.

The present invention contemplates exploiting the immunologic potential of the natural anti-Gal antibody, demonstrated in pig cartilage xenograft rejection, for the regression and/or destruction of tumour lesions, treated to display α-Gal epitopes and for targeting the tumour cell membranes to antigen presenting cells by anti-Gal antibody. It is believed that such treatment will convert the tumour lesions into in situ autologous tumour vaccines that elicit a systemic protective immune response against the metastatic tumour cells by similar mechanisms as those observed in rejection of pig cartilage in monkeys. It is further believed that the anti-Gal IgG molecules binding to tumour cells expressing α-Gal epitopes will target tumour cell membranes to antigen presenting cells for eliciting a protective anti-tumour immune response against the autologous tumour antigens expressed on the tumour cells in the treated lesion and also expressed on metastatic tumour cells.

Pharmaceutical Compositions

According to a first aspect of the invention, there is provided a pharmaceutical composition comprising α-Gal BOEL for use in the treatment of a tumour.

In one embodiment, the tumour is a solid tumour, myeloma, or a lymphoma. In a further embodiment, the tumour is a solid tumour. In an alternative embodiment, the tumour is a non-solid tumour.

In one embodiment, the tumour is a tumour originating from an organ selected from peritoneum, liver, pancreas, lung, urinary bladder, prostate, uterus, cervix, vagina, bone marrow, breast, skin, brain, lymph node, head and neck, stomach, intestine, colon, kidney, testis, and ovaries. In a further embodiment, the tumour is a tumour originating from an organ selected from peritoneum, liver, pancreas, lung, urinary bladder, prostate, uterus, cervix, vagina, breast, skin, brain, lymph node, head and neck, stomach, intestine, colon and ovaries.

In one embodiment, the tumour comprises a primary tumour and/or a metastasis. In a further embodiment, the tumour comprises a primary tumour. In an alternative embodiment, the tumour comprises a secondary tumour.

In one embodiment, the tumour comprises melanoma, sarcoma, glioma, or carcinoma cells. In a further embodiment, the tumour comprises melanoma or carcinoma cells, or a metastasis.

The composition may be prepared as an aqueous glycolipid preparation comprising α-Gal BOEL, wherein said preparation comprises glycolipid micelles.

In one embodiment, the composition additionally comprises one or more pharmaceutically acceptable carrier(s), diluent(s) and/or excipient(s). The carrier, diluent and/or excipient must be "pharmaceutically acceptable" in the sense of being compatible with the other ingredients of the composition and not deleterious to the recipient thereof. The person skilled in the art will appreciate aspects of pharmaceutical formulation which are exemplified for instance in Remington: The Science and Practice of Pharmacy; Pharmaceutical Press; $22^{nd}$ Edition; Allen, Loyd V. Ed. 2012, London, UK.

The composition of the invention may be prepared by combining α-Gal BOEL with standard pharmaceutical carriers or diluents according to conventional procedures well known in the art. These procedures may involve mixing, granulating and compressing or dissolving the ingredients as appropriate to the desired preparation.

In one embodiment, the pharmaceutical composition may also contain deoxycholate, or other mild detergents that may increase penetration of the glycolipids into cell membranes.

The pharmaceutical compositions of the invention may be formulated for administration by any route, and include those in a form adapted for oral, topical or parenteral administration to mammals including humans.

Therefore, in one embodiment, the composition is for administration by injection. In an alternative embodiment, the composition is a topical application, such as a topical ointment, topical lotion or topical solution.

In one embodiment, the composition is administered in one dose or multiple doses, such as multiple doses. In a further embodiment, the multiple doses are administered simultaneously (i.e. on one occasion). In a further alternative embodiment, the multiple doses are administered sequentially (i.e. on two or more separate occasions, such as during separate treatments).

When administration is sequential (i.e. on separate occasions), the composition may be administered when suitable time has elapsed between administrations, for example, 3 days, 5 days, a week, two weeks, a month, 2 months, 3 months, 6 months, or 12 months.

For parenteral administration, fluid unit dosage forms are prepared utilising the composition and a sterile vehicle, such as water. In preparing solutions the composition can be dissolved in water for injection and filter-sterilised before filling into a suitable vial or ampoule and sealing.

The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives and emollients in ointments and creams.

The formulations may also contain compatible conventional carriers, such as cream or ointment bases and ethanol or oleyl alcohol for lotions.

Combinations

It will be appreciated that the compound of the invention can be administered as the sole therapeutic agent or it can be administered in combination therapy with one of more other compounds (or therapies) for treatment of a tumour.

Thus, according to a further aspect of the invention there is provided a pharmaceutical composition comprising α-Gal BOEL in combination with one or more additional therapeutic agents.

For the treatment of a tumour, the compound of the invention may be advantageously employed in combination with one or more other medicinal agents, more particularly, with one or more anti-cancer agents or adjuvants (supporting agents in the therapy) in cancer therapy.

Examples of other therapeutic agents or treatments that may be administered together (whether concurrently or at different time intervals) with the compounds of the invention include but are not limited to:

Topoisomerase I inhibitors;
Antimetabolites;
Tubulin targeting agents;
DNA binder and topoisomerase II inhibitors;
Alkylating Agents;
Monoclonal Antibodies;
Anti-Hormones;
Signal Transduction Inhibitors;
Proteasome Inhibitors;
DNA methyl transferases;
Cytokines and retinoids;
Chromatin targeted therapies;
Radiotherapy; and
Other therapeutic or prophylactic agents.

Particular examples of anti-cancer agents or adjuvants (or salts thereof), include but are not limited to any of the agents selected from groups (i)-(xlvi), and optionally group (xlvii), below:

(i) Platinum compounds, for example cisplatin (optionally combined with amifostine), carboplatin or oxaliplatin;
(ii) Taxane compounds, for example paclitaxel, paclitaxel protein bound particles (Abraxane™), docetaxel, cabazitaxel or larotaxel;
(iii) Topoisomerase I inhibitors, for example camptothecin compounds, for example camptothecin, irinotecan (CPT11), SN-38, or topotecan;
(iv) Topoisomerase II inhibitors, for example anti-tumour epipodophyllotoxins or podophyllotoxin derivatives for example etoposide, or teniposide;
(v) Vinca alkaloids, for example vinblastine, vincristine, liposomal vincristine (Onco-TCS), vinorelbine, vindesine, vinflunine or vinvesir;
(vi) Nucleoside derivatives, for example 5-fluorouracil (5-FU, optionally in combination with leucovorin), gemcitabine, capecitabine, tegafur, UFT, S1, cladribine, cytarabine (Ara-C, cytosine arabinoside), fludarabine, clofarabine, or nelarabine;
(vii) Antimetabolites, for example clofarabine, aminopterin, or methotrexate, azacitidine, cytarabine, floxuridine, pentostatin, thioguanine, thiopurine, 6-mercaptopurine, or hydroxyurea (hydroxycarbamide);
(viii) Alkylating agents, such as nitrogen mustards or nitrosourea, for example cyclophosphamide, chlorambucil, carmustine (BCNU), bendamustine, thiotepa, melphalan, treosulfan, lomustine (CCNU), altretamine, busulfan, dacarbazine, estramustine, fotemustine, ifosfamide (optionally in combination with mesna), pipobroman, procarbazine, streptozocin, temozolomide, uracil, mechlorethamine, methylcyclohexylchloroethylnitrosurea, or nimustine (ACNU);
(ix) Anthracyclines, anthracenediones and related drugs, for example daunorubicin, doxorubicin (optionally in combination with dexrazoxane), liposomal formulations of doxorubicin (eg. Caelyx™, Myocet™, Doxil™), idarubicin, mitoxantrone, epirubicin, amsacrine, or valrubicin;

(x) Epothilones, for example ixabepilone, patupilone, BMS-310705, KOS-862 and ZK-EPO, epothilone A, epothilone B, desoxyepothilone B (also known as epothilone D or KOS-862), aza-epothilone B (also known as BMS-247550), aulimalide, isolaulimalide, or luetherobin;

(xi) DNA methyl transferase inhibitors, for example temozolomide, azacytidine or decitabine;

(xii) Antifolates, for example methotrexate, pemetrexed disodium, or raltitrexed; (xiii) Cytotoxic antibiotics, for example antinomycin D, bleomycin, mitomycin C, dactinomycin, carminomycin, daunomycin, levamisole, plicamycin, or mithramycin; (xiv) Tubulin-binding agents, for example combrestatin, colchicines or nocodazole; (xv) Signal Transduction inhibitors such as Kinase inhibitors (e.g. EGFR (epithelial growth factor receptor) inhibitors, VEGFR (vascular endothelial growth factor receptor) inhibitors, PDGFR (platelet-derived growth factor receptor) inhibitors, MTKI (multi target kinase inhibitors), Raf inhibitors, mTOR inhibitors for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), or vemurafenib (PLX4032/RG7204);

(xvi) Aurora kinase inhibitors for example AT9283, barasertib (AZD1152), TAK-901, MK0457 (VX680), cenisertib (R-763), danusertib (PHA-739358), alisertib (MLN-8237), or MP-470;

(xvii) CDK inhibitors for example AT7519, roscovitine, seliciclib, alvocidib (flavopiridol), dinaciclib (SCH-727965), 7-hydroxy-staurosporine (UCN-01), JNJ-7706621, BMS-387032 (a.k.a. SNS-032), PHA533533, PD332991, ZK-304709, or AZD-5438;

(xviii) PKA/B inhibitors and PKB (akt) pathway inhibitors for example AT13148, AZ-5363, Semaphore, SF1126 and MTOR inhibitors such as rapamycin analogues, AP23841 and AP23573, calmodulin inhibitors (forkhead translocation inhibitors), API-2/TCN (triciribine), RX-0201, enzastaurin HCl (LY317615), NL-71-101, SR-13668, PX-316, or KRX-0401 (perifosine/NSC 639966);

(xix) Hsp90 inhibitors for example AT13387, herbimycin, geldanamycin (GA), 17-allylamino-17-desmethoxygeldanamycin (17-AAG) e.g. NSC-330507, Kos-953 and CNF-1010, 17-dimethylaminoethylamino-17-demethoxygeldanamycin hydrochloride (17-DMAG) e.g. NSC-707545 and Kos-1022, NVP-AUY922 (VER-52296), NVP-BEP800, CNF-2024 (BIIB-021 an oral purine), ganetespib (STA-9090), SNX-5422 (SC-102112) or IPI-504;

(xx) Monoclonal Antibodies (unconjugated or conjugated to radioisotopes, toxins or other agents), antibody derivatives and related agents, such as anti-CD, anti-VEGFR, anti-HER2 or anti-EGFR antibodies, for example rituximab (CD20), ofatumumab (CD20), ibritumomab tiuxetan (CD20), GA101 (CD20), tositumomab (CD20), epratuzumab (CD22), lintuzumab (CD33), gemtuzumab ozogamicin (CD33), alemtuzumab (CD52), galiximab (CD80), trastuzumab (HER2 antibody), pertuzumab (HER2), trastuzumab-DM1 (HER2), ertumaxomab (HER2 and CD3), cetuximab (EGFR), panitumumab (EGFR), necitumumab (EGFR), nimotuzumab (EGFR), bevacizumab (VEGF), ipilimumab (CTLA4), catumaxumab (EpCAM and CD3), abagovomab (CA125), farletuzumab (folate receptor), elotuzumab (CS1), denosumab (RANK ligand), figitumumab (IGF1R), CP751,871 (IGF1R), mapatumumab (TRAIL receptor), metMAB (met), mitumomab (GD3 ganglioside), naptumomab estafenatox (5T4), or siltuximab (IL6);

(xxi) Estrogen receptor antagonists or selective estrogen receptor modulators (SERMs) or inhibitors of estrogen synthesis, for example tamoxifen, fulvestrant, toremifene, droloxifene, faslodex, or raloxifene;

(xxii) Aromatase inhibitors and related drugs, such as exemestane, anastrozole, letrazole, testolactone aminoglutethimide, mitotane or vorozole;

(xxiii) Antiandrogens (i.e. androgen receptor antagonists) and related agents for example bicalutamide, nilutamide, flutamide, cyproterone, or ketoconazole;

(xxiv) Hormones and analogues thereof such as medroxyprogesterone, diethylstilbestrol (a.k.a. diethylstilboestrol) or octreotide;

(xxv) Steroids for example dromostanolone propionate, megestrol acetate, nandrolone (decanoate, phenpropionate), fluoxymestrone or gossypol, (xxvi) Steroidal cytochrome P450 17alpha-hydroxylase-17, 20-lyase inhibitor (CYP17), e.g. abiraterone;

(xxvii) Gonadotropin releasing hormone agonists or antagonists (GnRAs) for example abarelix, goserelin acetate, histrelin acetate, leuprolide acetate, triptorelin, buserelin, or deslorelin;

(xxviii) Glucocorticoids, for example prednisone, prednisolone, dexamethasone;

(xxix) Differentiating agents, such as retinoids, rexinoids, vitamin D or retinoic acid and retinoic acid metabolism blocking agents (RAMBA) for example accutane, alitretinoin, bexarotene, or tretinoin;

(xxx) Farnesyltransferase inhibitors for example tipifarnib;

(xxxi) Chromatin targeted therapies such as histone deacetylase (HDAC) inhibitors for example sodium butyrate, suberoylanilide hydroxamide acid (SAHA), depsipeptide (FR 901228), dacinostat (NVP-LAQ824), R306465/JNJ-16241199, JNJ-26481585, trichostatin A, vorinostat, chlamydocin, A-173, JNJ-MGCD-0103, PXD-101, or apicidin; (xxxii) Proteasome Inhibitors for example bortezomib, carfilzomib, CEP-18770, MLN-9708, or ONX-0912;

(xxxiii) Photodynamic drugs for example porfimer sodium or temoporfin;

(xxxiv) Marine organism-derived anticancer agents such as trabectidin;

(xxxv) Radiolabelled drugs for radioimmunotherapy for example with a beta particle-emitting isotope (e.g., Iodine-131, Yittrium-90) or an alpha particle-emitting isotope (e.g., Bismuth-213 or Actinium-225) for example ibritumomab or Iodine tositumomab;

(xxxvi) Telomerase inhibitors for example telomestatin;

(xxxvii) Matrix metalloproteinase inhibitors for example batimastat, marimastat, prinostat or metastat;

(xxxviii) Recombinant interferons (such as interferon-γ and interferon α) and interleukins (e.g. interleukin 2), for example aldesleukin, denileukin diftitox, interferon alfa 2a, interferon alfa 2b, or peginterferon alfa 2b;

(xxxix) Selective immunoresponse modulators for example thalidomide, or lenalidomide;

(xl) Therapeutic Vaccines such as sipuleucel-T (Provenge) or OncoVex;

(xli) Cytokine-activating agents include Picibanil, Romurtide, Sizofiran, Virulizin, or Thymosin;

(xlii) Arsenic trioxide;

(xliii) Inhibitors of G-protein coupled receptors (GPCR) for example atrasentan;

(xliv) Enzymes such as L-asparaginase, pegaspargase, rasburicase, or pegademase;

(xlv) DNA repair inhibitors such as PARP inhibitors for example, olaparib, velaparib, iniparib, INO-1001, AG-014699, or ONO-2231;

(xlvi) Agonists of Death receptor (e.g. TNF-related apoptosis inducing ligand (TRAIL) receptor), such as mapatumumab (formerly HGS-ETR1), conatumumab (formerly AMG 655), PRO95780, lexatumumab, dulanermin, CS-1008, apomab or recombinant TRAIL ligands such as recombinant Human TRAIL/Apo2 Ligand;

(xlvii) Prophylactic agents (adjuncts); i.e. agents that reduce or alleviate some of the side effects associated with chemotherapy agents, for example
  anti-emetic agents,
  agents that prevent or decrease the duration of chemotherapy-associated neutropenia and prevent complications that arise from reduced levels of platelets, red blood cells or white blood cells, for example interleukin-11 (e.g. oprelvekin), erythropoietin (EPO) and analogues thereof (e.g. darbepoetin alfa), colony-stimulating factor analogs such as granulocyte macrophage-colony stimulating factor (GM-CSF) (e.g. sargramostim), and granulocyte-colony stimulating factor (G-CSF) and analogues thereof (e.g. filgrastim, pegfilgrastim),
  agents that inhibit bone resorption such as denosumab or bisphosphonates e.g. zoledronate, zoledronic acid, pamidronate and ibandronate,
  agents that suppress inflammatory responses such as dexamethasone, prednisone, and prednisolone,
  agents used to reduce blood levels of growth hormone and IGF-I (and other hormones) in patients with acromegaly or other rare hormone-producing tumours, such as synthetic forms of the hormone somatostatin e.g. octreotide acetate,
  antidote to drugs that decrease levels of folic acid such as leucovorin, or folinic acid,
  agents for pain e.g. opiates such as morphine, diamorphine and fentanyl,
  non-steroidal anti-inflammatory drugs (NSAID) such as COX-2 inhibitors for example celecoxib, etoricoxib and lumiracoxib,
  agents for mucositis e.g. palifermin,
  agents for the treatment of side-effects including anorexia, cachexia, oedema or thromoembolic episodes, such as megestrol acetate.

In one particular embodiment, the pharmaceutical composition additionally comprises one or more systemic inhibitors of immune system down-regulation. Examples of suitable systemic inhibitors of immune system down-regulation are described in US 2012/263677 and include anti-CTLA-4, PD-1 and PD-L1 antibodies.

In a yet further embodiment, the one or more systemic inhibitors of immune system down-regulation are selected from anti-PD-1 antibodies. Data is presented herein in Example 5 and FIG. 9 which demonstrates the synergistic properties of a combination of the compound of the invention (α-Gal BOEL) and an anti-PD-1 antibody with respect to preventing metastases growth as compared to α-Gal BOEL and anti-PD-1 alone.

In a further embodiment, the pharmaceutical composition additionally comprises one or more enhancers of immune system up-regulation. Examples of suitable enhancers of immune system up-regulation are described in US 2012/263677 and include suitable non-specific cytokines, such as interleukin-1, -2, or -6 (IL-1, IL-2 or IL-6) and aldesleukin; interferon-alpha or gamma (IFN-α and IFN-γ), interferon alfa-2b and pegylated interferon (including pegylated interferon alfa-2a and pegylated interferon alfa-2b); granulocyte macrophage colony stimulating factor (GM-CSF, molgramostim or sargramostim); dendritic cell vaccines and other allogeneic or autologous therapeutic cancer vaccines, including intralesional vaccines containing an oncolytic herpes virus encoding GM-CSF (OncoVex®) or a plasmid encoding human leukocyte antigen-B7 and beta-2 microglobulin agent designed to express allogeneic MHC class I antigens (Allovectin-7®); and antibodies against specific tumour antigens. In a yet further embodiment, the one or more enhancers of immune system up-regulation are selected from IL-2 and interferon-gamma.

Each of the compounds present in the combinations of the invention may be given in individually varying dose schedules and via different routes. For example, the α-Gal BOEL of the invention is intended to be administered directly to the tumour whereas the systemic inhibitors of immune system down-regulation, such as anti-PD-1 antibodies, will typically be delivered systemically, i.e. by intravenous injection. As such, the posology of each of the two or more agents may differ: each may be administered at the same time or at different times. A person skilled in the art would know through his or her common general knowledge the dosing regimes and combination therapies to use. For example, the compound of the invention may be using in combination with one or more other agents which are administered according to their existing combination regimen.

Methods of Treatment

According to a further aspect of the invention, there is provided a method of treating a tumour in a subject, comprising:
  a) providing:
    i) a subject comprising at least one tumour that comprises a plurality of cancer cells having a cell surface; and
    ii) the pharmaceutical composition as defined herein; and
  b) introducing the pharmaceutical composition into the tumour.

In one embodiment, the pharmaceutical composition induces an immune response to the tumour thereby treating the tumour.

In one embodiment, the invention provides a method for inducing an immune response to a tumour in a subject, comprising:
  a) administering to a subject comprising at least one tumour, an effective amount of a pharmaceutical composition comprising α-Gal BOEL to induce an immune response to the at least one tumour.

In one embodiment, the invention provides a method for treating a tumour in a subject, comprising:
  a) administering to a subject comprising at least one tumour, an effective amount of a pharmaceutical composition comprising α-Gal BOEL to induce an immune response to the at least one tumour,
    wherein inducing an immune response to the tumour results in a reduction in the tumour thereby treating the tumour in the subject.

In one embodiment, the composition further comprises at least one systemic inhibitor of immune system down-regulation.

In one embodiment, the at least one systemic inhibitor of immune system down-regulation is selected from anti-CTLA-4, PD-1 and PD-L1 antibodies.

In one embodiment, the method is repeated 1-5 times until the tumour is reduced in size.

In one embodiment, the method is repeated 1-5 times until the tumour is undetectable.

In one embodiment, the pharmaceutical composition is injected into a primary tumour and induces an immune response that is effective in treating at least one secondary tumour that arose from the primary tumour.

In one embodiment, the pharmaceutical composition is injected into a primary tumour, and induces an immune response that is effective in reducing the size of at least one secondary tumour that arose from the primary tumour.

In one embodiment, the method further comprises surgical removal of the tumour after inducing an immune response to the tumour.

In one embodiment, the method further comprises surgical removal of the tumour after administration of the pharmaceutical composition.

In one embodiment, the surgical removal of the tumour occurs between about 1-21 days after administration of the pharmaceutical composition.

In one embodiment, the surgical removal of the tumour occurs between about 1-14 days after administration of the pharmaceutical composition.

In one embodiment, the surgical removal of the tumour occurs between about 1-7 days after administration of the pharmaceutical composition.

In one embodiment, the surgical removal of the tumour occurs between about 7-14 days after administration of the pharmaceutical composition.

In one embodiment, the surgical removal of the tumour occurs between about 14-21 days after administration of the pharmaceutical composition.

The method of the invention allows for the administration of α-Gal BOEL in order to display an α-Gal epitope on the cell surface of the cancer cells.

In one embodiment, the method further comprises displaying a membrane-bound α-Gal epitope on said tumour cell.

In one embodiment, the present invention contemplates a method of treating a subject, comprising:
a) providing:
  i) a subject having endogenous anti-Gal antibody and a plurality of nonresectable tumours, wherein at least a subset of said tumours is accessible via a procedure selected from the group consisting of direct injection, injection by endoscopy, bronchoscopy, cystoscopy, colonoscopy, laparoscopy, and catheterization,
  ii) the pharmaceutical composition as defined herein; and
b) intratumourally injecting said composition using said procedure.

In one embodiment, the α-Gal epitope of α-Gal BOEL becomes opsonized. In one embodiment, the opsonized α-Gal epitope induces production of an autologous vaccine against said tumour by targeting tumour cells and cell membranes to antigen presenting cells.

In one embodiment, the subject is a human or a mouse. In one embodiment, the subject is a human. In an alternative embodiment, the subject is a mouse.

According to another aspect of the invention, there is provided a method of introducing α-Gal BOEL into a tumour in a mouse, comprising:
a) providing:
  i) a mouse, (1) lacking an α1,3galactosyltransferase gene, (2) having anti-Gal antibodies, and (3) comprising at least one tumour comprising a plurality of cancer cells having a cell surface; and
  ii) α-Gal BOEL; and
b) introducing α-Gal BOEL into at least one of said tumours to display an α-Gal epitope on the cell surface of the cancer cells.

Anti-Gal Targeting of Autologous Tumour Vaccines to Antigen Presenting Cells

It has been shown that α-Gal epitopes can be inserted in vitro into a tumour cell membrane by incubation of tumour cells with α-Gal glycolipids. The co-incubation of tumour cells or tumour cell membranes with such α-Gal glycolipids results in their spontaneous in vitro insertion into the tumour cell membranes and the expression of α-Gal epitopes on these cell membranes. Tumour cells engineered to express α-Gal epitopes by various molecular biology methods with the α1,3galactosyltransferase gene were studied as autologous tumour vaccines. Following their intradermal injection, the natural anti-Gal IgG antibody binds in situ at the vaccination site, to the α-Gal epitopes on the vaccinating tumour cell membrane and target the vaccine to antigen presenting cells. Although it is not necessary to understand the mechanism of an invention, it is believed that the binding of the Fc portion of the complexed anti-Gal to Fcγ receptors on antigen presenting cells induces effective uptake of the opsonized vaccinating tumour cell membranes into antigen presenting cells. Thus, the uncharacterized tumour antigens of the autologous tumour are also internalized into the antigen presenting cells. After transport of vaccinating autologous tumour membranes to the draining lymph nodes, the antigen presenting cells process and present the tumour antigen peptides for activation of tumour specific cytotoxic and helper T cells (i.e., $CD8^+$ and $CD4^+$ T cells, respectively).

A proof of principle for the efficacy of tumour vaccines expressing α-Gal epitopes was achieved in studies in a mouse experimental model immunized with melanoma cells expressing α-Gal epitopes and challenged with the same melanoma cells which, however, lack α-Gal epitopes (LaTemple D C et al. *Cancer Res.* 1999, 59: 3417-23, and Deriy L et al. *Cancer Gene Therapy* 2005; 12: 528-39). The mice used in those studies were knockout mice for the α1,3galactosyltransferase gene (i.e., these mice lack the α-Gal epitope and can produce the anti-Gal antibody). Mice immunized with melanoma cells engineered to express α-Gal epitopes displayed an effective immune protection against challenge with the same tumour cells, which however lack α-Gal epitopes. In contrast, mice immunized with tumour cells lacking α-Gal epitopes, did not display a protective immune response against challenge with the live tumour cells lacking α-Gal epitopes.

α-Gal Glycolipids in Tumour Therapy

The present invention contemplates the treatment of patients with solid tumour masses. Particular embodiments of the present invention contemplate novel immunotherapy treatments of cancer patients that aim to immunize the individual patient against his or her own tumour lesions by conversion of the patient's own tumour into an autologous tumour vaccine (see U.S. Pat. No. 5,879,675, herein incorporated by reference). For example, the '675 patent teaches an in vitro processing of tumour cells and/or cell membranes. Upon injection of these cells into a patient the vaccine is targeted by anti-Gal antibody to APCs and elicits a protective immune response against an autologous tumour antigen. Unlike the present invention, however, the '675 patent does not teach: i) an in vivo intratumoural treatment for the induction of inflammation, regression and/or destruction of the tumour by the natural anti-Gal antibody; or ii) the display of α-Gal epitopes on tumour cells in vivo following an intratumoural injection of α-Gal glycolipids within cancer patients.

In one embodiment of the present invention α-Gal glycolipids may be delivered into a tumour lesion comprising tumour cells by a non-surgical intratumoural injection (i.e., for example, by endoscopy, catheterization, or the like), or by any other method for in vivo introduction into tumours of the α-Gal glycolipids, or anti-Gal binding epitopes on various molecules.

Post-surgery recurrence of chemotherapy refractory metastases, is believed to be the most common cause of death in patients with solid tumours. High incidence of such relapsing metastases (80%) have been reported in patients with pancreatic and ovarian carcinomas and to a somewhat lesser extent in other solid tumours such as melanoma and colorectal, lung and breast carcinoma. Many of these relapsing patients are considered to have terminal disease, as no treatment is available for them, and they die within weeks or months after detection of the metastases.

In one embodiment, the present invention contemplates a therapeutic method for regression and/or destruction of tumour metastases by exploiting the fact that all humans, naturally produce the anti-Gal antibody as approximately 1% of their immunoglobulins. The immunological potential of the anti-Gal antibody can be harnessed to regress and/or destroy any tumour lesions and converting them into an in situ autologous tumour vaccine by intratumoural injection of glycolipids carrying the α-Gal epitope (i.e. α-Gal BOEL).

Therefore, the invention described herein may induce regression and/or destruction of the treated tumour lesions. Thus, in one embodiment, the treated tumour undergoes regression. In an alternative embodiment, the treated tumour is destroyed.

In a further embodiment, the tumour (i.e. which is displaying the α-Gal epitope) undergoes regression, wherein said tumour is selected from a melanoma or an organ metastasis, such as liver metastasis. In a further alternative embodiment, the tumour (i.e. which is displaying the α-Gal epitope) is destroyed, wherein said tumour is selected from a melanoma or an organ metastasis, such as liver metastasis.

In one embodiment, the introducing step causes regression of a second tumour in the subject as a result of the conversion of the treated tumour into an autologous tumour vaccine. In a further embodiment, said second tumour is selected from a melanoma or a liver metastasis.

In one embodiment, the introducing step causes destruction of a second tumour in the subject. In a further embodiment, said second tumour is selected from a melanoma or a liver metastasis.

Many α-Gal glycolipids will spontaneously insert into the tumour cell membranes, since the hydrophobic (i.e. lipophilic) lipid tail of the α-Gal glycolipids is in a more stable energetic form when embedded in the outer leaflet of the lipid bilayer of the cell membrane as compared to a water-surrounded micellular core. Spontaneous insertion (incorporation) of other types of glycolipids called gangliosides into cell membranes has been previously demonstrated (Kanda S et al. *J Biochem.* (Tokyo). 1982; 91: 1707-18, and Spiegel S et al. *J. Cell Biol.* 1985; 100: 721-26). The insertion of α-Gal glycolipids into the tumour cell membranes is expected to result in the de novo display of α-Gal epitopes on the cell membrane surface. α-Gal epitope expression may facilitate an anti-Gal antibody mediated regression and/or destruction of the tumour cells by such mechanisms which include, but are not limited to, complement mediated cytolysis (CDC) and antibody dependent cell mediated cytolysis (ADCC) and may also lead to tumour necrosis. An anti-Gal opsonized tumour cell membrane will then be effectively targeted by antigen presenting cells, thereby converting the treated tumour lesions into autologous tumour vaccines. This autologous vaccine will then stimulate the immune system to react against tumour antigens resulting in the further regression and/or destruction of tumour cells expressing these antigens within other tumour lesions and/or micrometastases of the treated patient.

In one embodiment, the subject was treated previously to surgically remove the tumour.

In an alternative embodiment, the subject was not treated previously to surgically remove the tumour, i.e., the method described herein may be performed as neo-adjuvant therapy several weeks prior to resection of the primary tumour. In one embodiment, an intratumoural injection of α-Gal BOEL, decreases the size of the tumour and converts the treated tumour into an autologous tumour vaccine. Although such a tumour will be eventually resected, it is believed that prior to its resection the treated tumour will elicit an immune response against micrometastases that display the same tumour antigens.

Mechanisms of Anti-Gal Antibody Tumour Regression and/or Destruction

Although it is not necessary to understand the mechanism of an invention, it is believed that tumour lesion regression and/or destruction by the injected α-Gal glycolipids may comprise a biochemical and physiological basis.

In one embodiment, the method further comprises inducing an intratumoural inflammation.

An intratumoural injection may result in a local rupture of tumour associated capillaries thereby providing natural anti-Gal IgM and anti-Gal IgG antibody molecules access to the tumour interior. Anti-Gal antibodies would then be able to interact with the α-Gal epitopes on α-Gal glycolipid micelles, or individual α-Gal glycolipids molecules, thereby inducing local activation of complement and generation of the complement cleavage chemotactic factors C5a and C3a. Moreover, C3b gets covalently deposited onto target cells. Complement activation then initiates a local inflammatory process facilitating intratumoural granulocytes, monocytes, macrophages and dendritic cell migration directed by the de novo produced C5a and C3a chemotactic factors within the treated tumour lesions. The inflammatory process may be further amplified as a result of the insertion of α-Gal glycolipids into cell membranes causing an anti-Gal activation of endothelial cells (Palmetshofer A et al. *Transplantation.* 1998; 65: 844-53; Palmetshofer A et al. *Transplantation.* 1998; 65: 971-8). Endothelial cell activation and overall tumour cell damage may result in local production of additional pro-inflammatory cytokines and chemokines. These locally secreted cytokines and chemokines induce additional migration of macrophages, dendritic cells, and subsequent migration of lymphocytes into the lesion injected with α-Gal glycolipids. This cellular migration is mediated by receptors to pro-inflammatory cytokines and chemokines on antigen presenting cells and on lymphocytes (Cravens P D and Lipsky P E *Immunol. Cell Biol.* 2002; 80: 497-505). This initial induction of an inflammatory response enables the immune system to overcome its general lack of ability to detect the "stealthy nature" of developing tumour lesions. This inflammation also enables the immune system to overcome the immunosuppressive microenvironment within solid tumour lesions that is induced by the local cytokine milieu, and which normally prevent lymphocytes from penetrating into the tumour (Malmberg K *J. Cancer Immunol. Immunother.* 2004; 53: 879-92; Lugade A A et al. *J. Immunol.* 2005; 174:7516-23).

Destruction of the tumour cells occurs by anti-Gal binding to α-Gal glycolipids inserted into cell membranes. α-Gal glycolipids injected into a tumour may spontaneously insert into the outer leaflet of the phospholipid bilayer of tumour cell membranes. The subsequent binding of anti-Gal IgM and/or anti-Gal IgG to the α-Gal epitopes on the inserted α-Gal glycolipid induces the regression and/or destruction of the treated tumour via complement dependent cytolysis (CDC). The binding of anti-Gal IgG molecules to these α-Gal epitopes also facilitates antibody dependent cell cytolysis (ADCC) of the tumour cells.

In one embodiment, the tumour undergoes regression and/or destruction via complement dependent cytolysis (CDC).

In one embodiment, the tumour undergoes regression and/or destruction via antibody dependent cell cytolysis (ADCC).

In complement dependent cytolysis, it is believed that anti-Gal IgG and/or IgM molecules binding to tumour cells expressing α-Gal epitopes (due to α-Gal glycolipid insertion) activate the complement system. Subsequently, the complement C5b-9 membrane attack complex is formed as a result of this complement activation, then "pokes" holes in the tumour cell membranes, resulting in tumour cell lysis. This complement dependent cytolysis is similarly found when pig endothelial cells are lysed, leading to hyperacute rejection of xenografts (Collins B H et al. *J. Immunol.* 1995; 154: 5500-10,). In ADCC the effector cells are granulocytes, macrophages, and NK cells. These cells are attracted to the lesion because of the anti-Gal induced inflammatory process. They bind via their Fcγ receptors (FcγR) to the Fc portion of anti-Gal IgG molecules which are bound to the α-Gal glycolipid inserted into the tumour cell membrane. Once attached to the tumour cells, these effector cells secrete their granzyme vesicles into the membrane contact areas generating holes in the tumour cell membrane, thus inducing the destruction of these tumour cells. The efficacy of anti-Gal IgG in inducing ADCC destruction of cells expressing α-Gal epitopes was demonstrated with xenograft pig cells binding anti-Gal via their α-Gal epitopes (Galili, U. *Immunol. Today* 1993, 14: 480-82). A similar anti-Gal mediated ADCC process occurs when tumour cells bind anti-Gal via α-Gal epitopes expressed on their cell surface membrane (Tanemura M et al. *J. Clin. Invest.* 2000; 105: 301-10).

The uptake of tumour cell membranes by antigen presenting cells may result in an induction of a protective immune response against autologous tumour antigens in order to regress and/or destroy chemotherapy refractive micrometastases. Anti-Gal IgG antibody bound to α-Gal epitopes on membrane inserted α-Gal glycolipids or C3b deposited on the target cells via anti-Gal dependent complement activation stimulates antigen presenting cells to internalize cell membranes expressing the tumour antigens (i.e., for example, tumour associated antigens, TAAs). The internalized tumour antigens can then be transported by the antigen presenting cells from the treated tumour lesion to the draining lymph nodes. These tumour antigens may then be further processed by the antigen presenting cells and presented as immunogenic tumour peptides that activate tumour specific T cells. This process results in the induction of a systemic protective anti-tumour immune response (i.e., for example, an autologous tumour vaccine). Therefore, tumour lesions injected with α-Gal glycolipids ultimately are converted into in situ autologous tumour vaccines that elicit an immune response against micrometastases expressing the tumour antigens as those in the treated tumour lesions.

As a clinical treatment modality, α-Gal glycolipids can be administered into cancer lesions by various methods including, but not limited to, an intradermal injection (i.e., for example, into a melanoma tumour); an endoscopic injection (i.e., for example, into colorectal intestinal metastases); a laparoscopic injection (i.e., for example, into abdominal ovarian, colon, gastric, liver, or pancreatic carcinoma metastases (e.g. on the peritoneum or in the liver)); a transcutaneous imaging guided needle injection (i.e., for example, into lung tumours); bronchoscopic injection (i.e., for example, into lung tumours); colonoscopic injection; or a cystoscopic injection (i.e., for example, into urinary bladder carcinomas).

Therefore, in one embodiment, the introducing comprises a procedure including, but not limited to, injection, imaging guided injection, endoscopy, bronchoscopy, cystoscopy, colonoscopy, laparoscopy and catheterization.

In one embodiment, the introducing comprises non-surgical intratumoural injection. For example, the introducing comprises a procedure selected from: intradermal injection, transcutaneous imaging guided injection, endoscopic injection, bronchoscopic injection, cytoscopic injection, colonoscopic injection and laproscopic injection.

In one embodiment, the α-Gal glycolipid (i.e. α-Gal BOEL) is injected in a pharmaceutically acceptable solution (i.e. a sterile solution) selected from the group including, but not limited to, phosphate buffered saline (PBS), saline, other aqueous solutions or other excipients Generally Recognized As Safe (GRAS). In one embodiment, the solution of α-Gal glycolipids may also contain deoxycholate, or other mild detergents that may increase penetration of the glycolipids into cell membranes.

In one embodiment, the present invention contemplates an intratumoural injection of α-Gal glycolipids (i.e. α-Gal BOEL) into primary tumours as a neo-adjuvant therapy provided before tumour resection surgery. In one embodiment, a rapid inflammatory response induced by the pre-surgical injection by an α-Gal glycolipid results in decreasing the tumour lesion size, as well as converting it into an in situ autologous tumour vaccine. Although it is not necessary to understand the mechanism of an invention, it is believed that the immune response to the treated tumour may ultimately help to induce the immune destruction of micrometastases that are not detectable at the time of surgical resection of primary tumours. It is further believed that pre-surgical administration may help in preventing recurrence of the disease due to immunological destruction of micrometastases resistant to conventional adjuvant therapy (i.e., for example, chemotherapy and radiation) and which express tumour antigens as does the primary tumour. Such neo-adjuvant therapy may be administered to any solid tumour or lymphoma that can be injected directly, or by guided imaging, or any other known method.

According to a further aspect of the invention, there is provided a kit comprising the pharmaceutical composition as defined herein, and optionally instructions to use said kit in accordance with the method as defined herein.

In one embodiment, the kit additionally comprises a delivery device, such as an intratumoural delivery device.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

The following examples are intended only as illustrative examples of embodiments of the invention. They are not to be considered as limiting the present invention.

Synthesis

In the description of the synthetic method described below and in the referenced synthetic methods that are used to prepare starting materials, it is to be understood that all proposed reaction conditions, including choice of solvent, reaction atmosphere, reaction temperature, duration of the experiment and workup procedures can be selected by a person skilled in the art. It is understood by one skilled in the art of organic synthesis that the functionality present on various portions of the molecule must be compatible with the reagents and conditions utilised. Necessary starting materials may be obtained by standard processes of organic chemistry, and are obtainable by analogous procedures to those illustrated and/or referenced within.

The reactions were performed with the use of commercial reagents (Acros, Aldrich, and Fluka); anhydrous solvents were purified according to the standard procedures. Column chromatography was performed on Silica gel 60 0.040-0.063 mm (Merck), gel filtration was carried out on Sephadex LH-20 (GE Healthcare) columns. Solvents were removed in vacuum at 30-40° C. Thin layer chromatography (TLC) was performed on Silica gel 60 F254 aluminium-backed plates (Merck). Spots of compounds were visualized by dipping a TLC plate into aqueous solution of $H_3PO_4$ (8%) and subsequent heating (>150° C.).

$^1$H NMR spectra were recorded on a Bruker BioSpin GmbH (700 MHz) spectrometer at 30° C.; chemical shifts ($\delta$, ppm) were referred to the peak of internal $D_2O$ ($\delta$ 4.750), $CDCl_3$ ($\delta$ 7.270), or $CD_3OD$ ($\delta$ 3.500); coupling constants (J) were measured in Hz. Signals of $^1$H NMR. Symbols of monosaccharide residues in NMR spectra for saccharides: I—β-GlcNAc (reducing end), II—β-Gal, III—α-Gal. MALDI TOF MS spectra were recorded on Bruker Daltonics Ultraflex MALDI TOF/TOF Mass Spectrometer (Germany).

The synthetic method described below may be used by one skilled in the art to prepare (9Z,9Z)-(2R)-3-(((2-(6-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexanamido)ethoxy)(hydroxy)phosphoryl)oxy)propane-1,2-diyl bis(octadec-9-enoate) (α-Gal BOEL).

Synthetic Scheme:

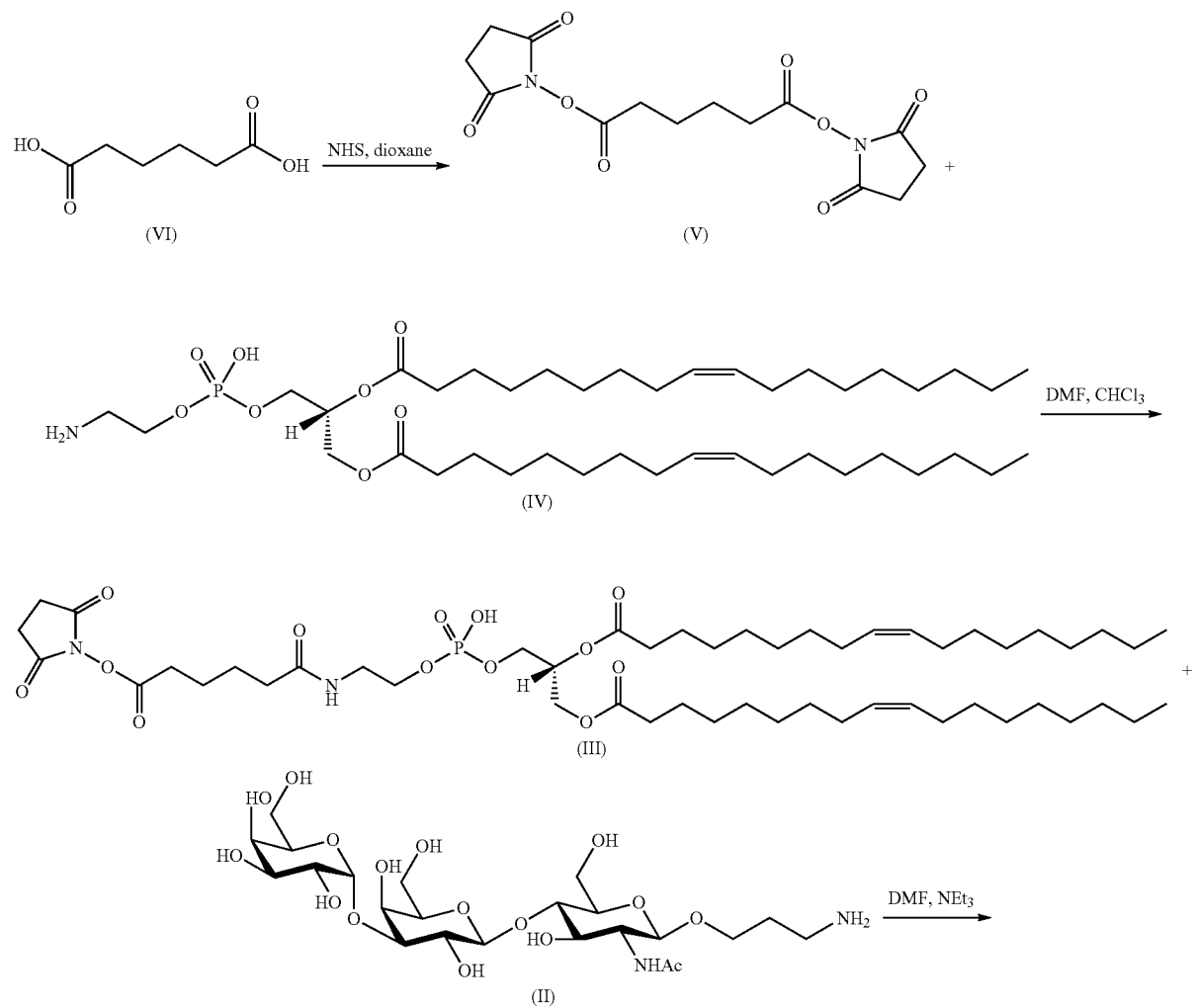

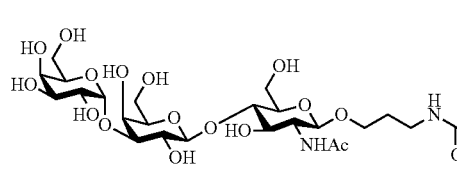 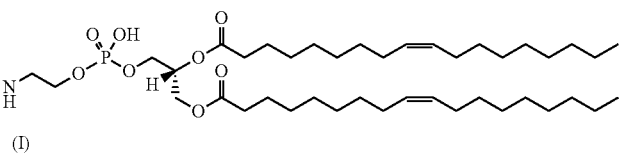

(I)

Preparation of (9Z,9'Z)-(2R)-3-(((2-(6-((3-(((2R,3R, 4R,5S,6R)-3-acetamido-5-(((2S,3R,4S,5S,6R)-3,5-dihydroxy-6-(hydroxymethyl)-4-(((2R,3R,4S,5R, 6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexanamido)ethoxy) (hydroxy)phosphoryl)oxy)propane-1,2-diyl bis (octadec-9-enoate)

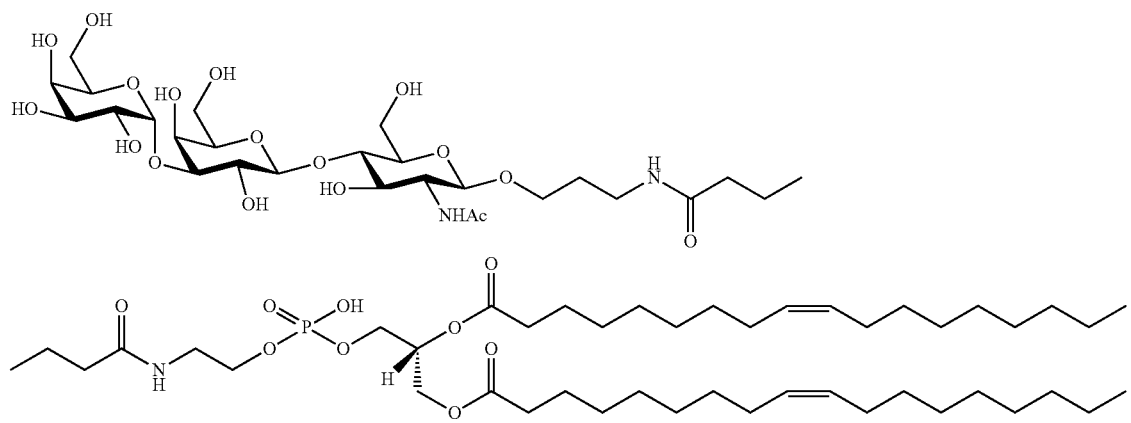

To a solution of 3-aminopropyl 4-O-[3-O-(α-D-Galactopyranosyl)-β-D-Galactopyranosyl]-2-acetamido-2-deoxy-β-D-glucopyranoside (II) (Mendeleev Communications, 2002, (143-145) or *Tetrahedron*, 61, (2005), 4313-4321, 52 mg, 0.086 mmol) in dry DMF (2 mL) was added 15 μL of Et₃N followed by a solution of DOPE-Ad-ONSu (III) (U.S. Pat. No. 8,013,131 B2, 100.6 mg, 1.00 mmol) in CH₂Cl₂ (2 mL). The reaction was stirred for 2 hours at room temperature followed by sequential column chromatography (the first on Sephadex LH-20, and the second on silica gel eluting with CH₂Cl₂-EtOH—H₂O; 6:5:1) to afford the title compound (1) (105.6 mg, 84%).

$R_f$ 0.5 (CH₂Cl₂-EtOH—H₂O; 6:5:1)

¹H NMR (700 MHz, CDCl₃-CD₃OD 1:1, 30° C.), δ, ppm, selected: 5.45-5.54 (m, 4H, 2×-C$\underline{H}$=C$\underline{H}$—), 5.34-5.43 (m, 1H, —OCH₂—C$\underline{H}$O—CH₂O—), 5.18 (d, 1H, $J_{1,2}$ 2.52, H-1$^{III}$), 4.61 (d, 1$\underline{H}$, $J_{1,2}$ 7.57, H-1$^{II}$), 4.60 (dd, 1H, J 2.87, J 12.00, C(O)OC$\underline{H}$HCHOCH₂O—), 4.56 (d, 1H, $J_{1,2}$ 8.39, H-1$^I$), 4.36 (dd, 1H, J 6.8, J 12.00, —C(O)OCH$\underline{H}$CHOCH₂O—), 4.19 (d, 1H, $J_{3,4}$ 2.48, H-4$^{II}$), 4.13-4.18 (m, 2H, —CHO—C$\underline{H}_2$OP—), 3.52-3.62 (m, 3H, PO—CH₂—C$\underline{H}_2$—NH, —CH₂—CH$\underline{H}$—NH), 3.29-3.35 (m, 1H, —CH₂—C$\underline{H}$H—NH), 2.45-2.52 (m, 4H, 2×-C$\underline{H}_2$—CO), 2.36-2.45 (m, 4H, 2×-C$\underline{H}_2$—CO), 2.14-2.22 (m, 11H, 2×(—CH₂—CH=CH—C$\underline{H}_2$—), NHC(O)C$\underline{H}_3$), 1.85-1.96 (m, 2H, O—CH₂C$\underline{H}_2$CH₂—NH), 1.73-1.84 (m, 8H, COC$\underline{H}_2$CH₂CH₂C$\underline{H}_2$CO and 2×(COC$\underline{H}_2$C$\underline{H}_2$—), 1.36-1.55 (m, 40H, 20C$\underline{H}_2$), 1.05 (t, 6H, J 6.98, 2C$\underline{H}_3$).

C70H126N3O26P; MALDI MS: m/z 1480 (M Na+H); 1496 (MK+H); 1502 (MNa+Na), 1518 (M Na+K)

Example 1: ELISA to Demonstrate Binding to Anti-Gal Antibodies

A 96-well plate is first coated with α-Gal BOEL (obtained from Sigma as FSL-Galili(tri)™, Catalogue No. F9432). 50 μL PBS is added to each well. α-Gal BOEL is resuspended in PBS to a concentration of 2 mg/ml and 50 μL added to a well. Serial dilutions are performed by transferring 50 μL into wells across the plate making sure that each well is thoroughly mixed before transfer. The plate is left overnight to dry. This results in strong adherence of α-Gal BOEL to the wells by the L (lipid) portion of this molecule.

150 μL of blocking buffer (1×PBS/1% BSA) is added to the dry wells. The plate is covered and incubated at 37° C. for 2 hours. The well contents are discarded and the wells washed with PBS. 50 μL of the primary anti-Gal antibody (monoclonal mouse anti-Gal IgM in this example, M86 hybridoma supernatant) is added to each well. The plate is incubated at room temperature for 2 hours. The plate is washed 3 times with 200 μL washing buffer (1×PBS, 0.05% Tween).

50 μL of secondary goat anti-mouse IgM-HRP solution (Accurate Chemical; Catalogue No. JGM035020) is added to each well. The plate is covered and incubated at room temperature for 1 hour and then is washed 3 times with 200 μL washing buffer. 100 μL of a standard OPD (o-Phenylenediamine dihydrochloride) solution (e.g. Sigma; Catalogue No. P8287) is added to each well, incubated for 5 minutes and then 50 μL of stop solution (1 M sulfuric acid) is added. The well absorbances are immediately read at 492 nm ($A_{492}$) (see FIG. 2).

Figure 2:
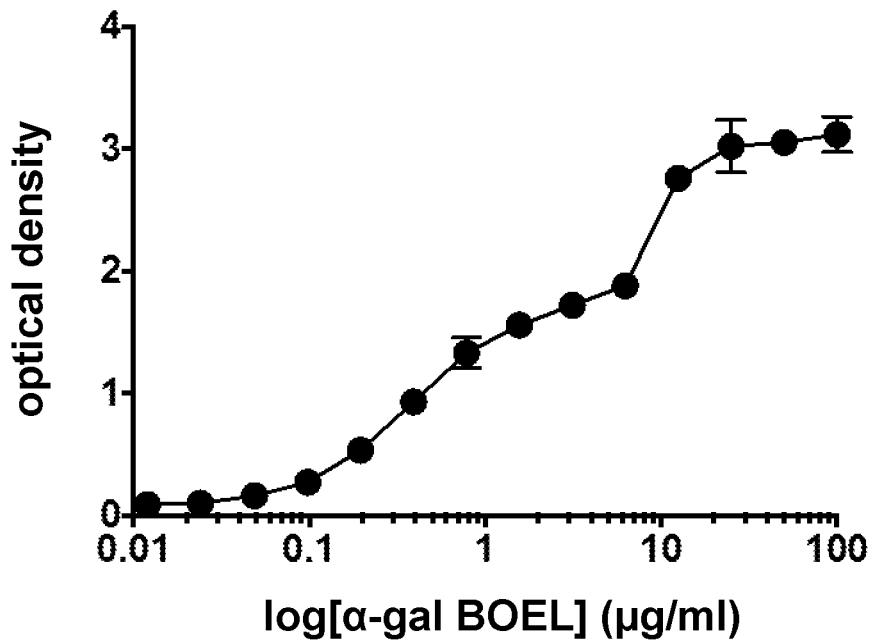
FIG. 2: Data to demonstrate that α-Gal BOEL binds to anti-Gal antibodies.

FIG. 2 shows the increase in $A_{492}$ as the amount of α-Gal BOEL is increased across the ELISA plate. The direct correlation between the increased amount of α-Gal BOEL bound to the ELISA wells and the increased binding of the monoclonal anti-Gal antibody to these ELISA wells indicates that this antibody binds to α-Gal epitopes on the α-Gal BOEL molecules dried in the wells.

Example 2: Complement-Dependent Cytotoxicity and Incorporation Assays

The assays below quantify both the amount of α-Gal BOEL inserted into the cell plasma membranes and the functional impact of α-Gal BOEL insertion in stimulating anti-Gal mediated complement-dependent cytotoxicity (CDC). α-Gal BOEL is titrated and incubated with CHO-K1 cells. These cells are either fixed and used in a whole cell ELISA assay, to determine incorporation of α-Gal into membranes, or incubated with anti-Gal antibody and human serum to measure CDC (or general cytotoxicity in the absence of complement from human serum).

α-Gal BOEL Titration and CHO-K1 Cell Preparation

α-Gal BOEL is titrated as follows. One 40 µl aliquot of α-Gal BOEL (2 mg/ml (obtained from Sigma as FSL-Galili (tri)™, Catalogue No. F9432)) is thawed and sonicated for 30 seconds. 40 µl of phosphate buffered saline (PBS) is added to the tube and vortexed for 10 seconds. 25 µl of this mix is added to 55 µl of PBS and mixed well. These dilutions are repeated to give a full titration of α-Gal BOEL in the desired concentration range.

CHO-K1 cells, which lack α-Gal epitopes, are resuspended in Dulbecco's PBS (DPBS) at 37° C. and centrifuged at 1000 rpm for 5 minutes. The supernatant is aspirated and the cell pellet resuspended to $1 \times 10^7$ cells/ml in 450 µl DPBS (37° C.). The cell pellet is washed again to remove all traces of serum.

Incubation of CHO-K1 Cells with α-Gal BOEL

An aliquot of the cell suspension (45 µl) is transferred to all tubes of α-Gal BOEL and mixed gently by inversion and incubated for 30 minutes at 37° C. The cells are washed thoroughly to remove excess unincorporated α-Gal BOEL. The tubes are centrifuged at 200×g for 5 minutes and cell pellet washed with 900 µl of warm DPBS, centrifuged again at 200×g for 5 minutes and resuspended in 250 µl of warm media. The cell suspension (25 µl) is transferred either to an assay plate (standard white 96-well plate for luminescence readout (available from Corning)) to perform the CDC assay (A) or 50 µl transferred to a poly-d-lysine coated plate (available from Sigma) for the in-cell ELISA (B) to measure incorporation into cell membranes.

Complement Dependent Cell Cytotoxicity/Cell Lysis (CDC) Assay

Anti-Gal antibody (from a range of sources, mouse anti-Gal containing plasma in this example) is added (25 µl/well) to the CDC assay plate (A) and then incubated for 30 minutes at 37° C. The assay plate is incubated for a further 30 minutes at 37° C. on a heated centrifuge tube block. The human serum (containing active complement) is diluted in warm media (to a pre-determined level by titration in the assay) and 50 µl added to each well. The plate is incubated at 37° C. for 30 minutes. The plate is removed from the incubator and allowed to equilibrate at room temperature for 15 minutes. 100 µl of the CellTiterGlo reagent (Promega, G7572) is added to each well of the plate. This reagent luminescence is proportional to the amount of ATP released from lysed cells. The plate is covered with foil and incubated on a plate shaker (400 rpm) for 2 minutes. Luminescence output is measured using a standard 96-well plate reader (see FIG. 3).

Figure 4:
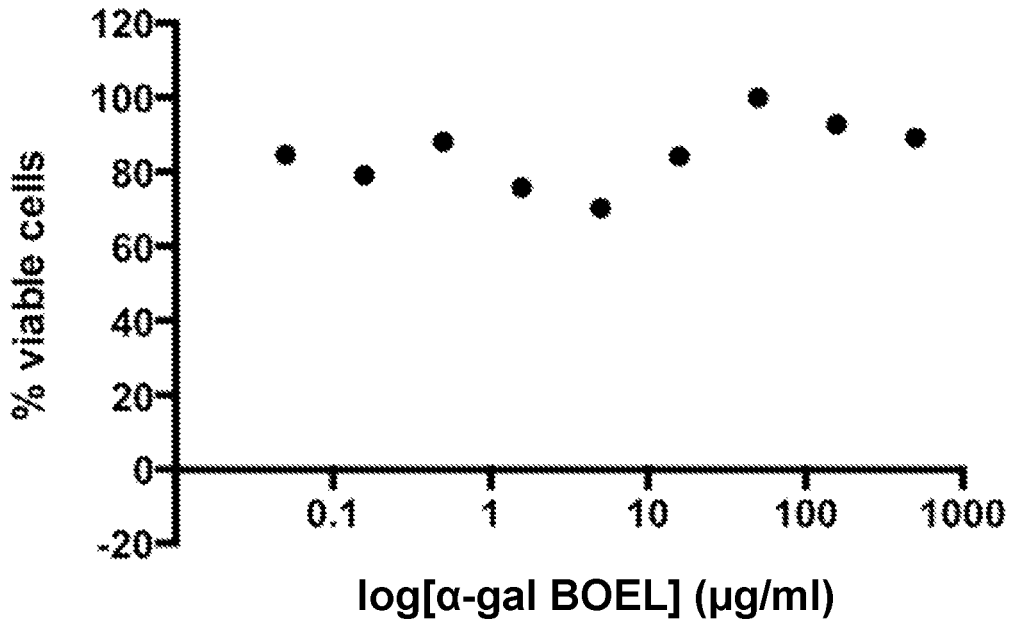
FIG. 4: Data to demonstrate that incorporation of α-Gal BOEL does not cause overt cytotoxicity to cells in the absence of complement.

General cellular toxicity was measured by following the CDC assay procedure above but replacing human serum with pre-warmed media. The level of cell death was measured by adding 100 µl CellTitreGlo reagent to each well in exactly the same manner as for the CDC assay above (see FIG. 4).

Figure 3:
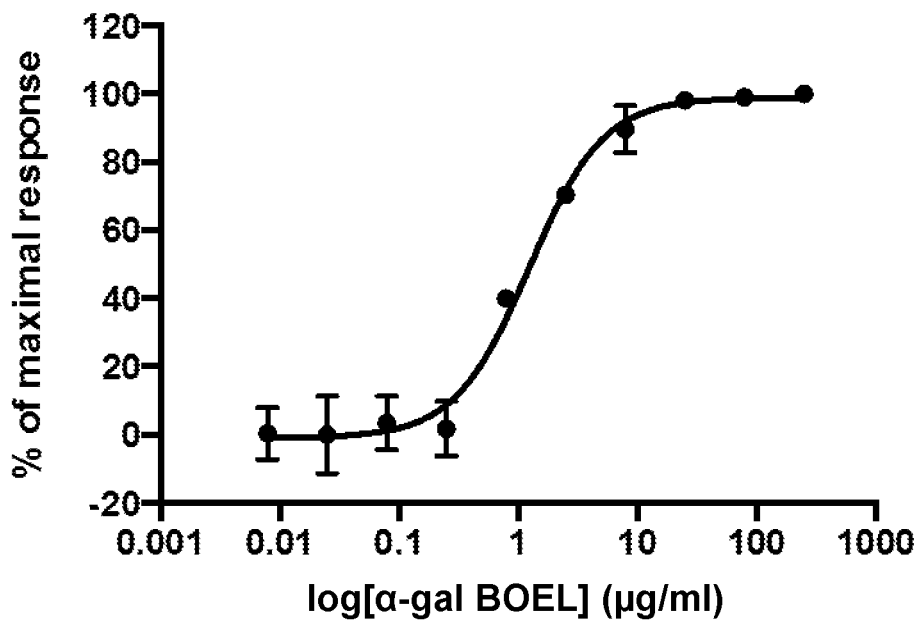
FIG. 3: Data to demonstrate that α-Gal BOEL induces complement mediated cell lysis of cancer cells.

FIG. 3 shows the inhibition of complement dependent cell lysis by increasing doses of α-Gal BOEL. As the dose of α-Gal BOEL is increased, the cell viability as measured by CellTitreGlo, increases due to the blocking of complement components from binding to the cells and lysing them. This blocking in mediated by α-Gal BOEL micelles binding anti-Gal in the solution and activating the complement cascade in the solution, causing complement consumption, thereby inhibiting complement mediated lysis of cells expressing α-Gal epitopes. If complement is inactivated no cell death occurs. In the absence of human serum, α-Gal BOEL has no impact on cell viability (FIG. 4) up to 500 µg/ml. Table 1 describes the EC50 value (the concentration of α-Gal BOEL that gives half-maximum response) for the inhibition of CDC by α-Gal BOEL over 4 independent experiments. The mean EC50 value is 1.35 µg/ml+/−1.48. No overt cytotoxicity is observed up to 500 µg/ml.

TABLE 1

Results from CDC assay

| Experiment | Date Tested | EC50 (µg/ml) |
|---|---|---|
| 1 | Jun. 2, 2014 | 1.36 |
| 2 | Jun. 2, 2014 | 1.24 |
| 3 | 19 Mar. 2014 | 1.38 |
| 4 | 22 Apr. 2014 | 1.43 |
| | Geomean | 1.35 |

In-Cell ELISA to Measure Incorporation of α-Gal BOEL into Cells

To measure incorporation of α-Gal BOEL into CHO-K1 cells, 50 µl of the CHO-K1 cell suspension containing α-Gal BOEL is transferred to a Poly-D-Lysine coated clear 96-well plate (B). The plate is spun at 1,000 rpm for 5 minutes. To fix the cells the media is removed and 100 µL of 4% formaldehyde added to each well. The plate is incubated in a fume hood at room temperature for 15 minutes. The formaldehyde is removed and the plate washed twice with 100 µL/well of 1× Tris Buffered Saline (TBS). An in-cell ELISA kit (In Cell ELISA colorimetric assay kit, 62200 Pierce Ltd) is used to measure level of the incorporation of α-Gal BOEL.

The TBS is removed and 100 µL/well of Quenching Solution added and incubated at room temperature for 20 minutes. The Quenching Solution is removed and the plate washed once with 100 µL/well of 1×TBS.

100 µL/well of Blocking Buffer added and incubate at room temperature for 30 minutes. Blocking Buffer is removed and 50 µL/well of diluted primary antibody added (M86 hybridoma supernatant in this example, titrated to find the optimum concentration). A plate sealer is applied and the plate is incubated overnight at 4° C. The primary antibody solution is removed and the plate washed three times with 100 µL/well of 1× Wash Buffer.

100 µL/well of HRP-conjugated goat anti-human (or mouse) IgG+IgM+IgA secondary antibody is added. The plate is incubated for 30 minutes at room temperature. The plate is washed three times with 200 µL/well of 1× Wash Buffer.

100 µL/well of TMB Substrate is added the plate incubated at room temperature, protected from light. The reaction is stopped by adding 100 µl/well of TMB stop solution within 15 minutes (or when the desired blue colour has been achieved). The absorbance at 450 nm is measured within 30 minutes of stopping the reaction (see FIG. 5).

Figure 5:
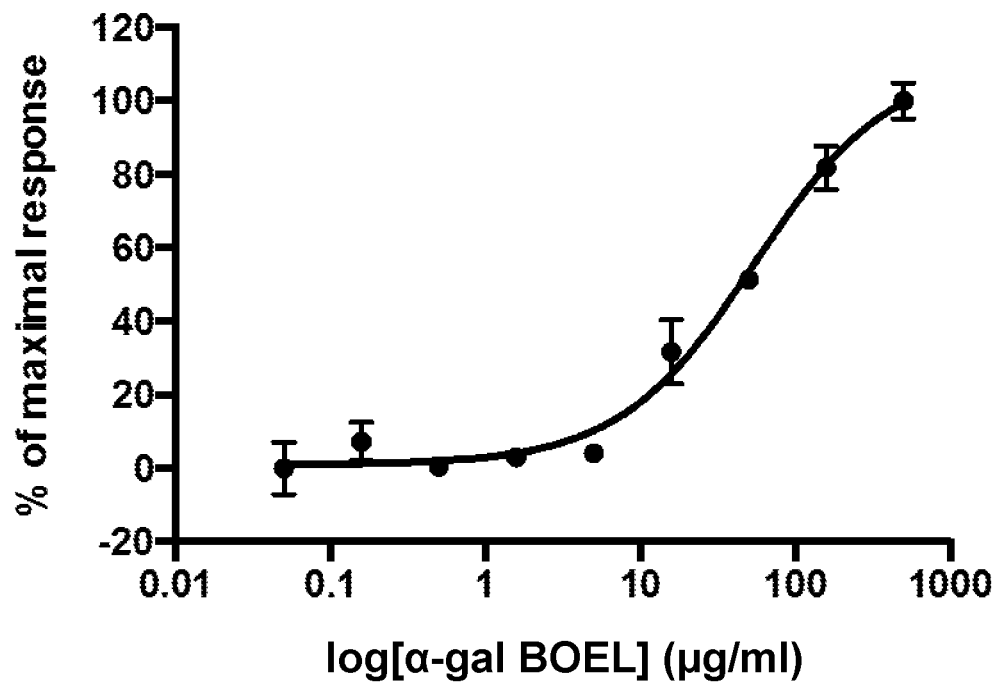
FIG. 5: Data to demonstrate that α-Gal BOEL incorporates into tumour cells.

It can be seen from FIG. 5 that α-Gal BOEL can be detected on the surface of CHO-K1 cells after incubation as described above.

Example 3: Complement Deposition Assays $1 \times 10^6$ B16-F10 and CHO-K1 cells were harvested from growing cultures and incubated with 500 µg/ml αGal BOEL in PBS for 1 hour at 37° C., after which the cells were washed 3 times with PBS. After washing the CHO-K1 cells were incubated with either 2.5% normal (NHS) or heat-inactivated (HI NHS) human serum for 10 minutes at 37° C. The B16-F10 cells were incubated with either 2.5% serum from normal GT−/− mice (NMS) or 2.5% serum from pig kidney homogenate immunised mice (I NMS) for 10 minutes at 37° C. The cells were placed on ice and washed twice with ice-cold cell staining buffer (PBS+0.1% BSA). The cells were incubated with either anti-C3b (C3b, Pierce MAI-70054, diluted 1:1000 in cell staining buffer) or anti-SC5b-9 (MAC, Quidel A239, diluted 1:100 in cell staining buffer) for 30 minutes on ice. The cells were washed twice with ice cold cell staining buffer and incubated with FITC goat anti-mouse IgG (Abcam ab97022, diluted 1:2000 in cell staining buffer) for 30 minutes on ice. After 2 further washes with ice-cold cell staining buffer the cells were resuspended in ice-cold cell staining buffer plus 7-AAD (Biolegend 420403). The cells were analysed using a Beckman Coulter Cytomics FC500 flow cytometer, with data captured in the FL-1 channel. Data on the histograms presented are gated on live cells.

Figure 6:
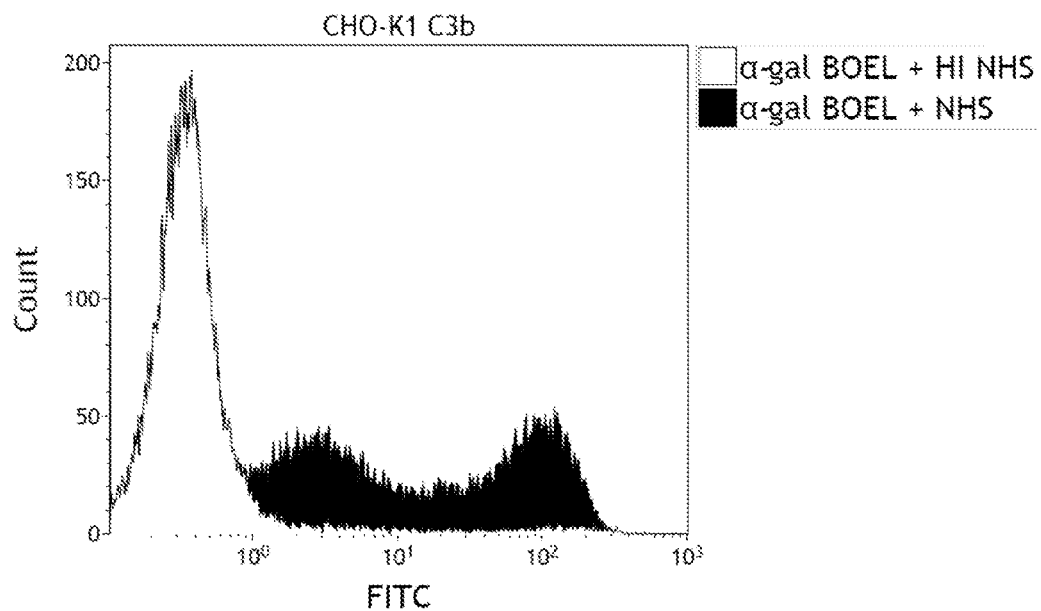
FIG. 6: Data to demonstrate that incorporation of α-Gal BOEL leads to deposition of the complement proteins C3b and MAC from human serum onto tumour cells.
Figure 6:
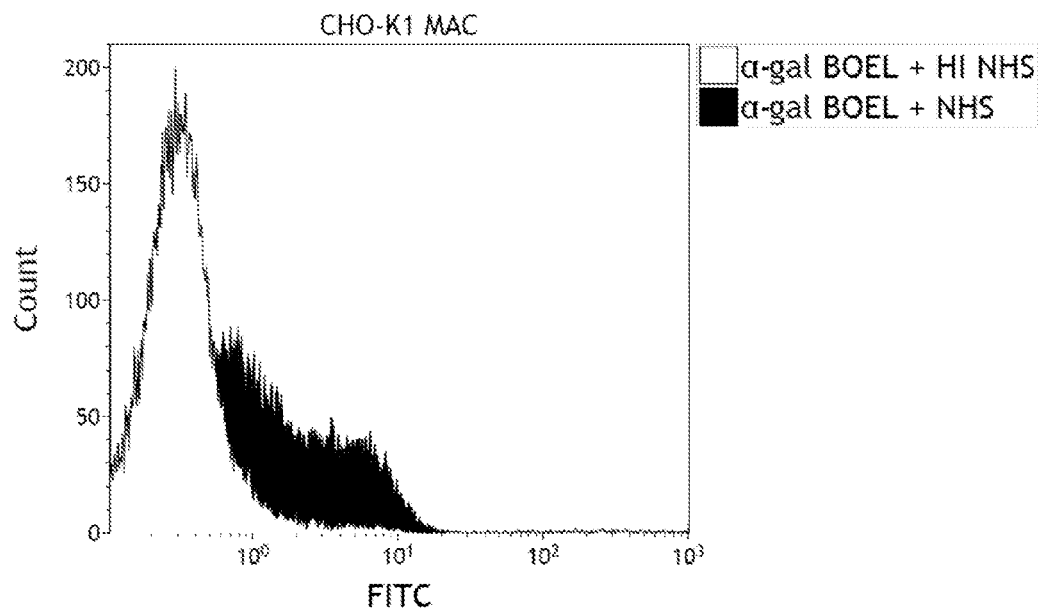

FIG. 6 demonstrates that incorporation of α-Gal BOEL leads to the deposition of complement proteins C3b and MAC from human or mouse serum onto the surface of CHO K1 (A&B) and B16 mouse melanoma cells (C&D).

Example 4: In Vivo Activity of α-Gal BOEL in α1,3-Galactosyltransferase Knockout (GT KO) Mouse Melanoma Model In vivo pharmacodynamics experiments were conducted to assess the effects of α-Gal BOEL in a GT KO mouse melanoma model with B16-F10 melanoma cells. The GT KO mouse strain was selected, because it, like humans, does not express the α-Gal antigen. As a result, the GT KO mice can be immunized with pig kidney membrane homogenate to produce titers of IgG and IgM anti-Gal antibodies that are similar to those seen naturally in humans. Such an immune response is induced since pig kidney membranes contain a high concentration of α-Gal epitopes on cell membranes and in intercellular matrix. B16-F10 cells were used since they are the only known murine cell that does not express α-Gal epitopes.

Figure 7:
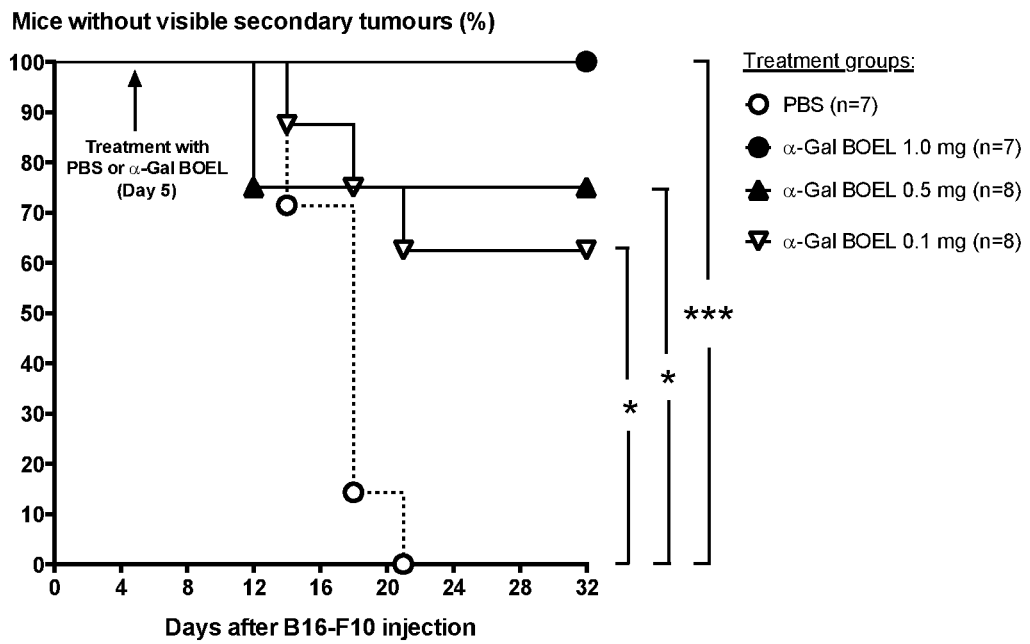
FIG. 7: Dose titration experiments with α-Gal BOEL. Anti-Gal producing GT KO mice were injected with $1\times10^6$ B16-F10 melanoma cells for primary tumour growth on their right flanks and $1\times10^4$ B16-F10 cells for secondary/distal tumour injection on the opposite flank. 5 days later, the main tumours were intra-tumourally treated with PBS (open circles), or 0.1 mg α-Gal BOEL (open triangles), or 0.5 mg α-Gal BOEL (closed triangles), or 1 mg of α-Gal BOEL (closed circles). The development of visible distal tumours as model for metastases development was followed for up to 32 days. The percentages of mice without visible distal tumours are plotted in the graphs. Statistical differences between the groups were determined by log-rank test.

In the B16-F10 melanoma model, mice were injected with cultured B16-F10 cells on both flanks, on one side they were injected with $1 \times 10^6$ melanoma cells to create a primary tumour and with a reduced cell number on the contra-lateral flank ($1 \times 10^4$ melanoma cells) to create a model of a 'distant metastasis' also referred to as secondary tumour. Primary tumours are injected intratumourally with α-Gal BOEL or vehicle control when a predefined tumour diameter is reached. The critical endpoint recorded is growth of the 'distant' tumour; this is used to measure the ability of an agent to elicit an effective protective anti-tumour immune response throughout the body. Doses from 0.1-2.5 mg of α-Gal BOEL were tested. When 0.1-mg to 1-mg α-Gal BOEL doses in 100 µL vehicle were tested side-by-side in the B16-F10 model, a dose-dependent activity response of α-Gal BOEL was observed. As exemplified in FIG. 7, 1 mg α-Gal BOEL consistently conferred a higher degree of protection than 0.1-mg and 0.5-mg doses.

Figure 8:
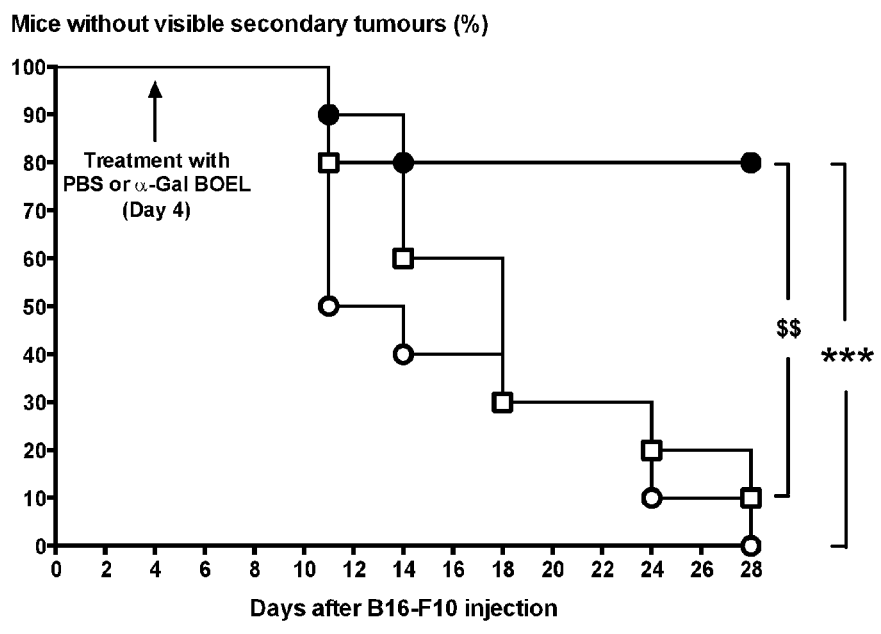
FIG. 8: α-Gal BOEL activity in anti-Gal producing mice (i.e mice immunized with pig kidney membranes) or mice lacking anti-Gal (i.e. non-immunized mice). Hyper-immunized or non-immunized GT KO mice were injected with $1\times10^6$ B16-F10 cells for primary tumour growth on their right flanks and either $1\times10^4$ B16-F10 cells for secondary/distal tumour injection on the opposite flank. 4 days later, the main tumours were intra-tumourally treated with PBS in hyper-immunized mice (open circles), or 1 mg α-Gal BOEL (closed circles for hyper-immunized mice; open squares for non-immunized mice). The development of visible distal tumours as model for metastases development was followed for up to 28 days. The percentages of mice without visible distal tumours are plotted in the graph. Statistical differences between the groups were determined by log-rank test.

It has also been shown that immunization of the GT KO mice with pig kidney membrane homogenate induces production of anti-Gal IgG and IgM antibodies that are necessary to confer α-Gal BOEL mediated protection from distal tumour development in the B16-F10 melanoma model. As can be seen in FIG. 8, 1 mg α-Gal BOEL protected 80% of anti-Gal producing GT KO mice from secondary tumour development. In contrast, 1 mg α-Gal BOEL lacked protective activity in non-immunized GT KO mice (i.e. mice lacking anti-Gal). These observations indicate that the α-Gal BOEL mediated induction of a protective anti-tumour immune response against development of distant metastases is dependent on the presence of anti-Gal in the treated subject. In the absence of anti-Gal, no significant protective anti-tumour immune response is observed.

Example 5: α-Gal BOEL and Anti-PD-1 Antibody Combinations Show Superior In Vivo Activity Over Anti-PD-1 Antibodies Alone Several lines of evidence suggest that two receptors, PD-1 and CTLA-4, on T cells function as checkpoints negatively regulate anti-tumour immune responses. At the same time, standard of care antibody drugs targeting PD-1 and CTLA-4 are showing promise for the treatment of advanced melanoma in clinical trials. It was tested if the anti-tumour effect of synthetic glycolipid α-Gal BOEL can be enhanced in combination with immunologic checkpoint inhibitors, namely anti-PD-1 monoclonal antibodies (mAbs) in the above described GT KO mouse melanoma model. It is assumed that the initial proliferation of tumour specific T cells, induced by antigen presenting cells that present processed tumour antigen peptides, may be enhanced by the inhibition of immunological checkpoints such as the anti-PD1 monoclonal antibodies. Thus, it is contemplated that combined treatment of tumour bearing subjects with both α-Gal BOEL and anti-PD1 antibody will be more effective than subjects treated only with one of these two treatments.

Figure 9:
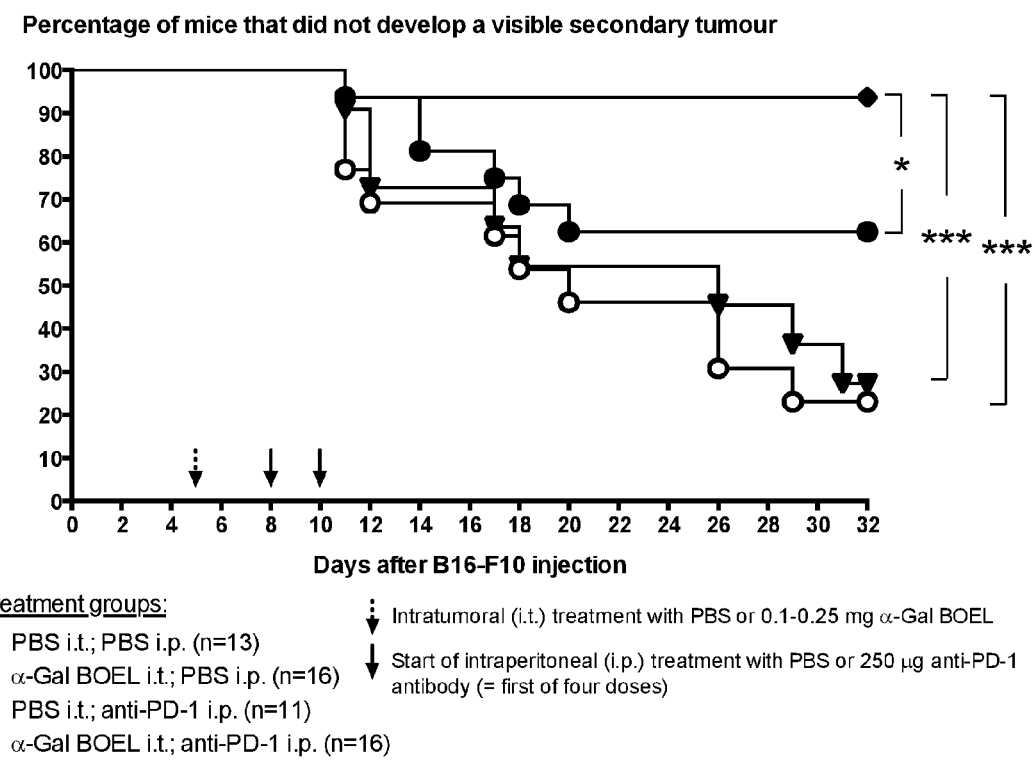
FIG. 9: α-Gal BOEL combination with anti-PD-1 shows superior activity in B16-F10 melanoma model. Anti-Gal producing GT KO mice were injected with $1\times10^6$ B16-F10 cells for primary tumour growth on their right flanks and $1\times10^4$ B16-F10 cells for secondary/distal tumour injection on the opposite flank. 5 days later, the main tumours were intra-tumourally (i.t.) treated with 100 μL PBS or 0.1 and 0.25 mg α-Gal BOEL in 100 μL PBS. On Day 8 or Day 10, mice were intraperitoneally (i.p.) treated with 200 μL PBS or 250 μg anti-PD-1 in 200 μL PBS. The i.p. treatment was repeated 3 times in three to four day intervals. The development of visible secondary/distal tumours as a model for metastases development was followed for up to 32 days. The percentages of mice without visible distal tumours are plotted in the graphs. Statistical differences between the treatment groups were determined by log-rank test. A combination of α-Gal BOEL i.t./anti-PD-1 i.p. (Closed diamonds) showed a statistically significant superior activity over α-Gal BOEL i.t./PBS i.p. (Closed circles; *, p<0.05), as well as over PBS i.t./anti-PD-1 i.p. (Closed triangles; *, p=0.0003), and over PBS i.t./PBS i.p. (Open circles; *, p<0.0001). The results of two independent experiments were combined for the graph.

To study this assumption, mice were challenged with $10^6$ B16-F10 tumour cells in one flank to create a primary tumour and $10^4$ B16-F10 cells in the contralateral flank to induce metastases-like secondary tumours. Five days after tumour cell injection, the primary tumours were treated intratumourally only with 0.1 and 0.25 mg α-Gal BOEL (instead of 1.0 mg in the experiment in FIG. 7), or PBS (=vehicle control). At Day 8 or Day 10, mice were intraperitoneally treated with 250 µg anti-PD-1 monoclonal antibody RMP1-14 (Biolegend (Catalogue No. 114102)) or with PBS. Of note, clone RMP1-14 was used in several studies to investigate anti-PD-1 effects in tumour models. The treatment with anti-PD-1 or vehicle was repeated three times in each experiment (mice received a total of four 250-µg doses). As can be seen in FIG. 9, a combination of α-Gal BOEL with the anti-PD-1 antibody had superior activity in terms of preventing growth of distant metastases as compared to α-Gal BOEL and anti-PD-1 alone. This indicated that anti-PD-1 synergizes with α-Gal BOEL in eliciting a protective anti-tumour immune response that is more potent than that observed in treatments using either α-Gal BOEL or anti-PD1 antibody alone.

The invention claimed is:

1. A method of treating a tumor in a subject, comprising: introducing into the tumor a pharmaceutical composition comprising (9Z,9'Z)-(2R)-3-(((2-(6-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexanamido)ethoxy)(hydroxy)phosphoryl)oxy)propane-1,2-diyl bis(octadec-9-enoate).

2. The method as defined in claim 1, wherein the subject is a human or a mouse.

3. The method as defined in claim 1, wherein the introducing step comprises a procedure selected from: injection, imaging guided injection, endoscopy, bronchoscopy, cystoscopy, colonoscopy, laparoscopy, and catheterization.

4. The method as defined in claim 1, wherein the subject was treated previously to surgically remove the tumor.

5. The method as defined in claim 1, wherein the subject was not treated previously to remove the tumor.

6. The method as defined in claim 1, wherein said pharmaceutical composition is introduced in an amount such that the tumor undergoes regression or is destroyed.

7. The method as defined in claim 1, wherein the tumor is a solid tumor, myeloma, or a lymphoma.

8. The method as defined in claim 1, wherein the tumor is a tumor originating from an organ selected from peritoneum, liver, pancreas, lung, urinary bladder, prostate, uterus, cervix, vagina, bone marrow, breast, skin, brain, lymph node, head and neck, stomach, intestine, colon, kidney, testis, and ovaries.

9. The method as defined in claim 1, wherein the tumor comprises a primary tumor and/or a metastasis.

10. The method as defined in claim 1, wherein the tumor comprises melanoma, sarcoma, glioma, or carcinoma cells.

11. The method as defined in claim 1, wherein the introducing step comprises administering the composition by injection.

12. The method as defined in claim 1, wherein introducing step comprises administering the composition in one dose or multiple doses.

13. The method as defined in claim 1, wherein the introducing step comprises administering the composition by topical application.

14. The method as defined in claim 13, wherein the composition is a topical ointment, topical lotion or topical solution.

15. The method as defined in claim 1, wherein the composition additionally comprises one or more pharmaceutically acceptable carrier(s), diluents(s) and/or excipient(s).

16. The method as defined in claim 1, wherein the composition additionally comprises one or more additional therapeutic agents.

17. The method defined in claim 16, wherein the one or more additional therapeutic agents comprise one or more systemic inhibitors of immune system down-regulation.

18. The method as defined in claim 17, wherein the one or more systemic inhibitors of immune system down-regulation is selected from anti-CTLA-4, PD-1 or PD-L1 antibodies.

* * * * *

UNITED STATES PATENT AND TRADEMARK OFFICE
CERTIFICATE OF CORRECTION

PATENT NO.        : 10,092,586 B2
APPLICATION NO.   : 15/310074
DATED             : October 9, 2018
INVENTOR(S)       : Uri Galili et al.

Page 1 of 1

It is certified that error appears in the above-identified patent and that said Letters Patent is hereby corrected as shown below:

In the Specification

Column 3, Line 30 "formation" should be amended to "formulation"
Column 4, Line 13 "as model" should be amended to "as a model"
Column 4, Line 28 "as model" should be amended to "as a model"
Column 4, Line 33 "in B16" should be amended to "in the B16"
Column 6, Line 63 "maybe" should be amended to "may be"
Column 9, Line 6 "glycoproteins. (Galili" should be amended to "glycoproteins (Galili"
Column 14, Line 28 ", dexamethasone" should be amended to ", or dexamethasone"
Column 14, Line 63 "include" should be amended to "including"
Column 16, Line 28 "using" should be amended to "used"
Column 28, Line 12 "blocking in mediated" should be amended to "blocking is mediated"

In the Claims

Claim 12, Column 32, Line 11 the text reading: "The method as defined in claim 1, wherein introducing step comprises administering the composition in one dose or multiple doses." should be replaced with "The method as defined in claim 1, wherein the introducing step comprises administering the composition in multiple doses."
Claim 17, Column 32, Line 26 the text reading: "The method defined in claim 16" should be replaced with "The method as defined in claim 16"

Signed and Sealed this
Nineteenth Day of February, 2019

Andrei Iancu
*Director of the United States Patent and Trademark Office*